United States Patent
Wilson et al.

(10) Patent No.: US 10,292,888 B2
(45) Date of Patent: May 21, 2019

(54) BRIDGE DEVICE FOR A PATIENT POSITIONING SYSTEM

(71) Applicant: MEDTEC, INC., Orange City, IA (US)

(72) Inventors: Roger F. Wilson, Sarasota, FL (US); Travis De Jong, Orange City, IA (US); William Barnat, Mount Holly, NJ (US); Bruce Ribble, Swisher, IA (US); Keith Van Voorst, Hull, IA (US)

(73) Assignee: MEDTEC, INC., Orange City, IA (US)

( * ) Notice: Subject to any disclaimer, the term of this patent is extended or adjusted under 35 U.S.C. 154(b) by 262 days.

(21) Appl. No.: 14/570,434

(22) Filed: Dec. 15, 2014

(65) Prior Publication Data

US 2015/0164725 A1 Jun. 18, 2015

Related U.S. Application Data

(60) Provisional application No. 61/917,666, filed on Dec. 18, 2013.

(51) Int. Cl.
*A61G 13/00* (2006.01)
*A61G 13/12* (2006.01)
(Continued)

(52) U.S. Cl.
CPC .......... *A61G 13/122* (2013.01); *A61B 6/0421* (2013.01); *A61B 90/14* (2016.02);
(Continued)

(58) Field of Classification Search
CPC .. A61G 13/101; A61G 13/122; A61G 13/129; A61G 13/123; A61G 13/121;
(Continued)

(56) References Cited

U.S. PATENT DOCUMENTS 1,891,755 A * 12/1932 Davis ...................... A61G 13/12
602/39
2,437,940 A * 3/1948 Cramer .................... A47C 3/26
248/407
(Continued)

FOREIGN PATENT DOCUMENTS

EP 1366714 A2 12/2003
WO 0143592 A1 6/2001
(Continued)

OTHER PUBLICATIONS

International Search Report for PCT/US2014/070798 dated Mar. 31, 2015.
(Continued)

*Primary Examiner* — Keri J Nelson
*Assistant Examiner* — Adam Baker
(74) *Attorney, Agent, or Firm* — Snyder, Clark, Lesch & Chung, LLP

(57) ABSTRACT

A bridge assembly is described for use with a patient positioning system including a patient support panel. The panel includes a pair of side rails extending along a central longitudinal axis of the panel. The bridge assembly is configured to be releasably secured via respective clamps at any position along the side rails and includes a pair of side sections and a central section connected between the side sections. The length of each side sections can be adjusted independently to enable the distance of the central section at each of the side sections from the patient support panel to be individually established. The central section can also be adjusted laterally with respect to the central longitudinal axis of the patient support panel.

19 Claims, 24 Drawing Sheets

(51) Int. Cl.
*A61G 13/10* (2006.01)
*A61B 6/04* (2006.01)
*A61N 5/10* (2006.01)
*A61B 90/14* (2016.01)
*A61B 90/57* (2016.01)
*A61B 90/50* (2016.01)

(52) U.S. Cl.
CPC ......... *A61G 13/101* (2013.01); *A61G 13/129* (2013.01); *A61N 5/1049* (2013.01); *A61B 2090/508* (2016.02); *A61B 2090/571* (2016.02); *A61N 2005/1097* (2013.01)

(58) Field of Classification Search
CPC ........ A61G 13/1255; A61G 2013/0072; A61G 2013/0054; A61G 1/013; A61G 1/04; A61G 15/10; A61G 7/08; A61G 13/1245; A61G 13/125; A61B 90/14; A61B 2090/571; A61B 2090/508; A61N 2005/1097; A61F 5/3769
USPC .............................. 128/870, 845; 5/601, 621
See application file for complete search history.

(56) References Cited

U.S. PATENT DOCUMENTS

| | | | | |
|---|---|---|---|---|
| 2,446,470 A * | 8/1948 | Godwin | ................ | A61G 13/12 128/845 |
| 2,789,625 A * | 4/1957 | Christie | ................. | A47C 1/10 297/410 |
| 3,063,447 A * | 11/1962 | Kirsten | ................. | A61G 13/12 128/876 |
| 3,530,515 A * | 9/1970 | Jacoby | ................ | A61G 7/0501 128/200.24 |
| 3,759,252 A * | 9/1973 | Berman | .................... | A61F 5/01 5/603 |
| 3,840,221 A | 10/1974 | Hogan | | |
| 5,242,455 A * | 9/1993 | Skeens | .................... | A61B 90/11 600/415 |
| 5,454,993 A | 10/1995 | Kostich | | |
| 5,681,326 A * | 10/1997 | Lax | ...................... | A61B 5/0555 378/163 |
| 5,832,550 A | 11/1998 | Hauger et al. | | |
| 6,161,237 A | 12/2000 | Tang et al. | | |
| 6,622,324 B2 | 9/2003 | VanSteenburg et al. | | |
| 7,060,046 B2 * | 6/2006 | Tanaka | .................. | A61F 5/0193 5/621 |
| 7,569,021 B2 * | 8/2009 | Sebelius | .............. | A61H 31/008 601/108 |
| 8,002,720 B2 * | 8/2011 | Hansen | .................. | A61H 31/00 601/107 |
| 8,146,599 B2 | 4/2012 | Wilson et al. | | |
| 2009/0308400 A1 * | 12/2009 | Wilson | .................. | A61F 5/3769 128/845 |
| 2012/0011653 A1 * | 1/2012 | Coppens | .................. | A61B 6/00 5/601 |
| 2015/0366438 A1 * | 12/2015 | Wilson | ............... | A61B 1/00009 600/102 |

FOREIGN PATENT DOCUMENTS

| | | |
|---|---|---|
| WO | 2006081412 A2 | 8/2006 |
| WO | 2009/155211 A1 | 12/2009 |
| WO | 2012/009728 A2 | 1/2012 |

OTHER PUBLICATIONS

International Search Report for Application No. PCT/US2009/047154 dated Oct. 7, 2009.

* cited by examiner

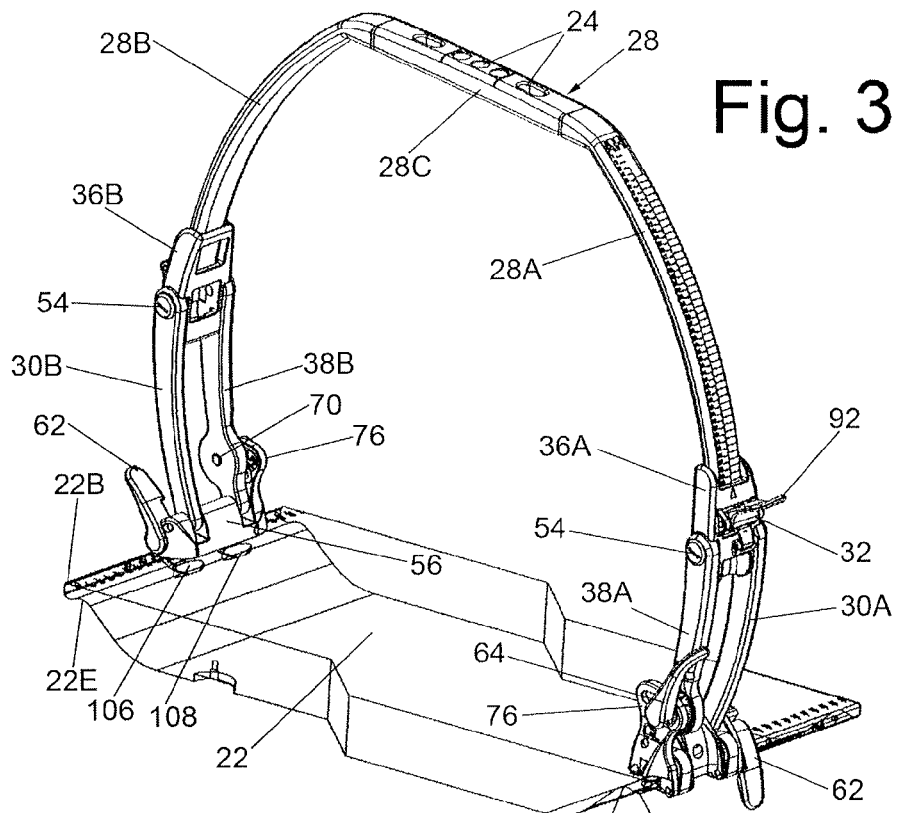
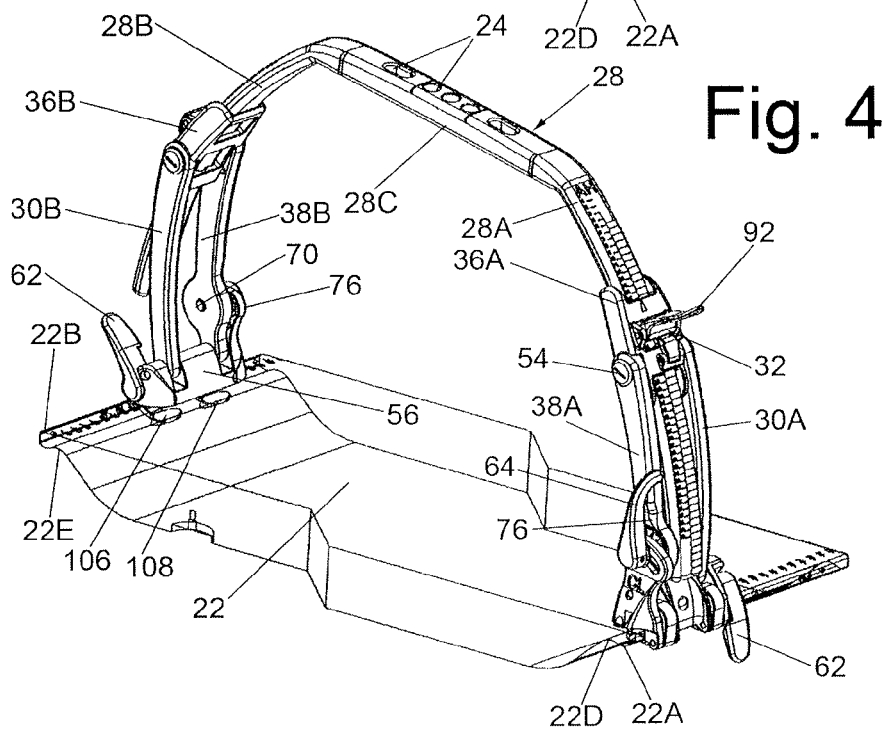

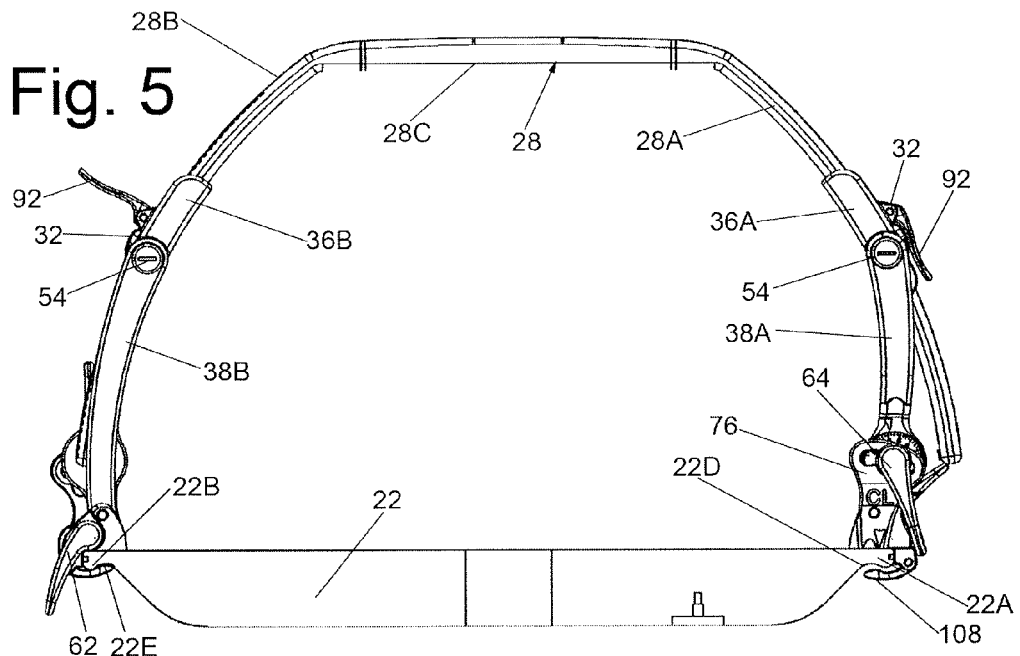
Fig. 5
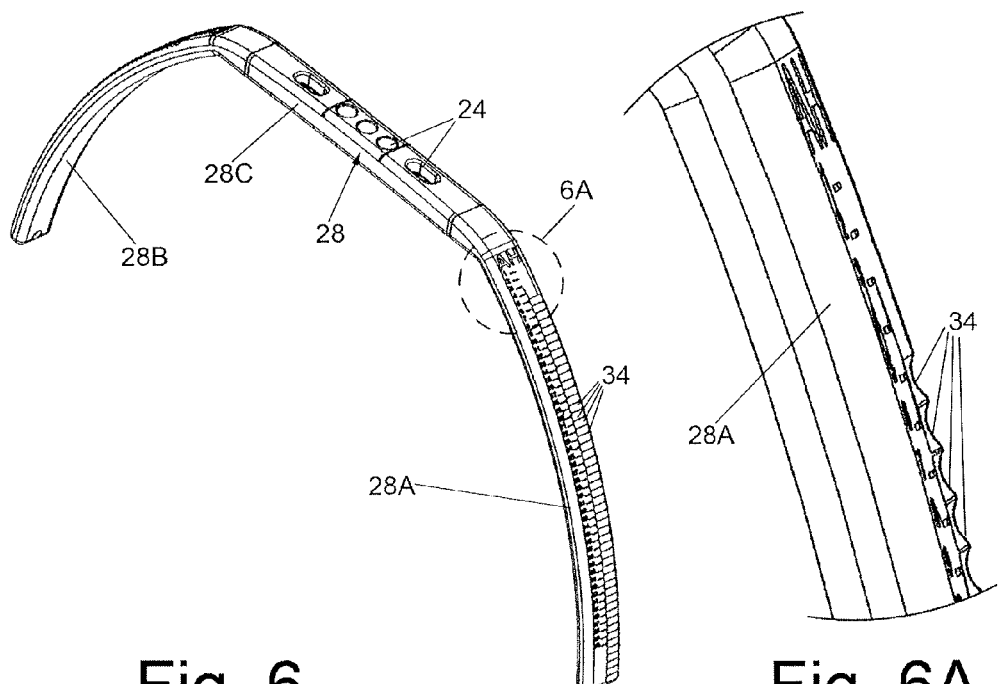
Fig. 6
Fig. 6A

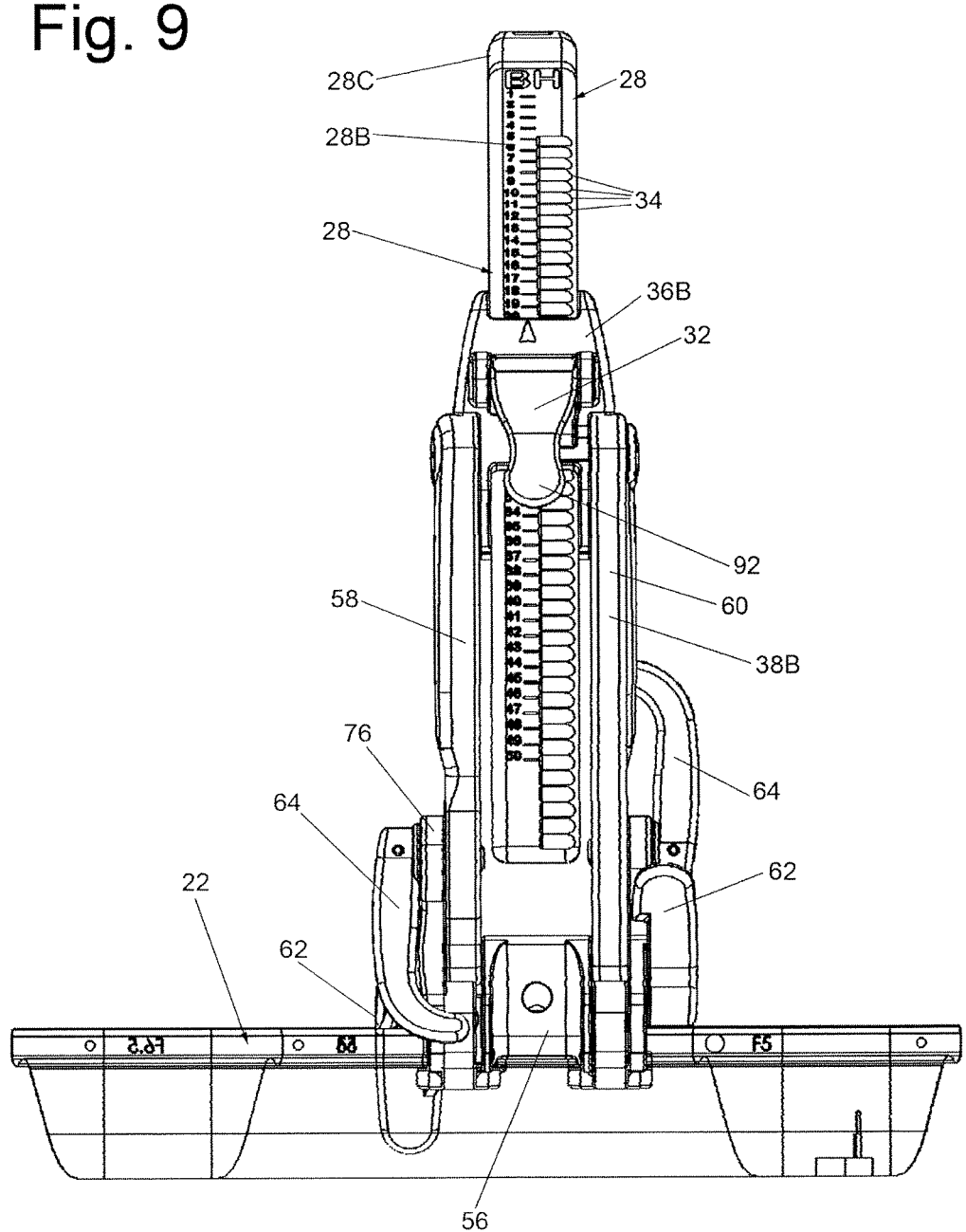

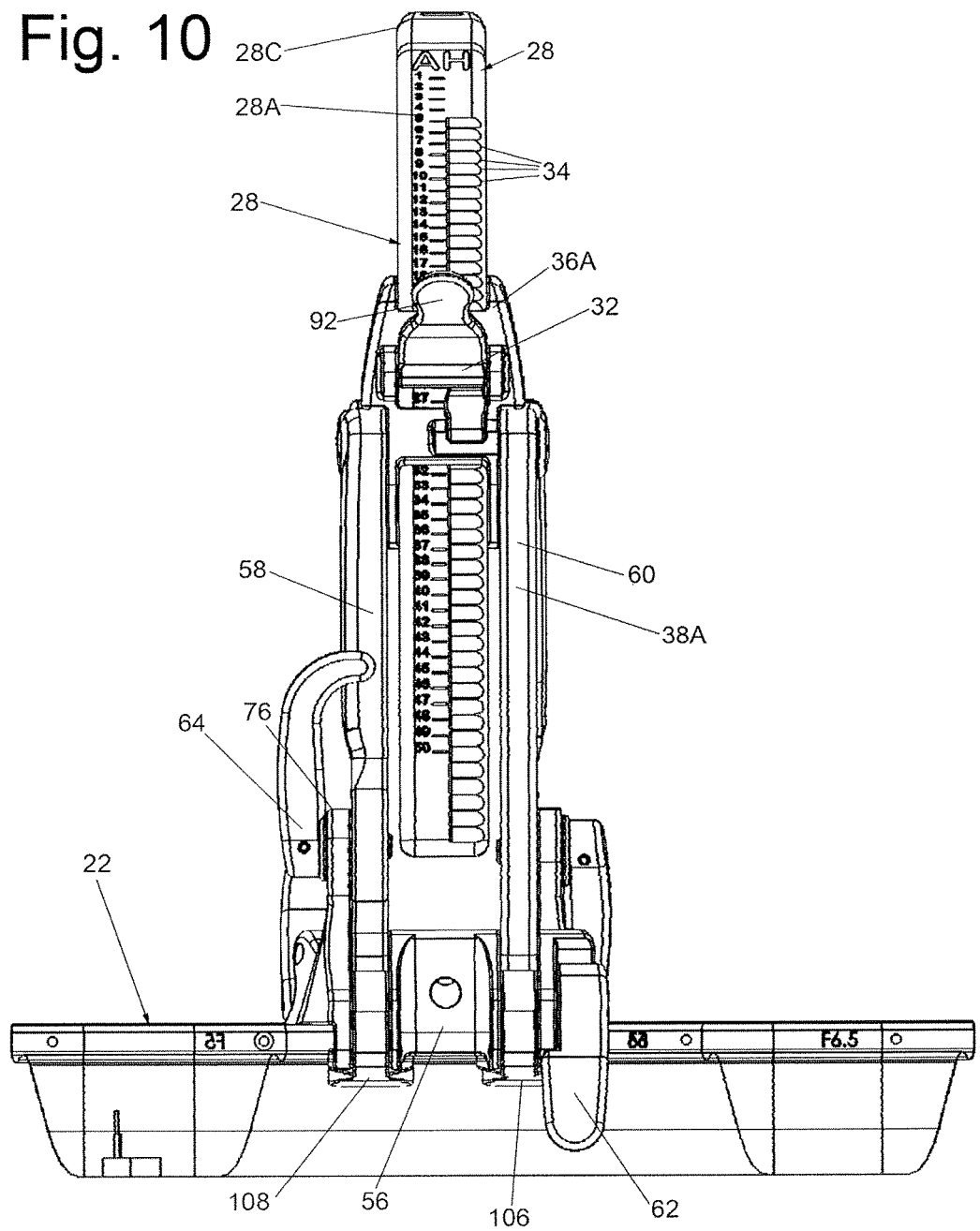

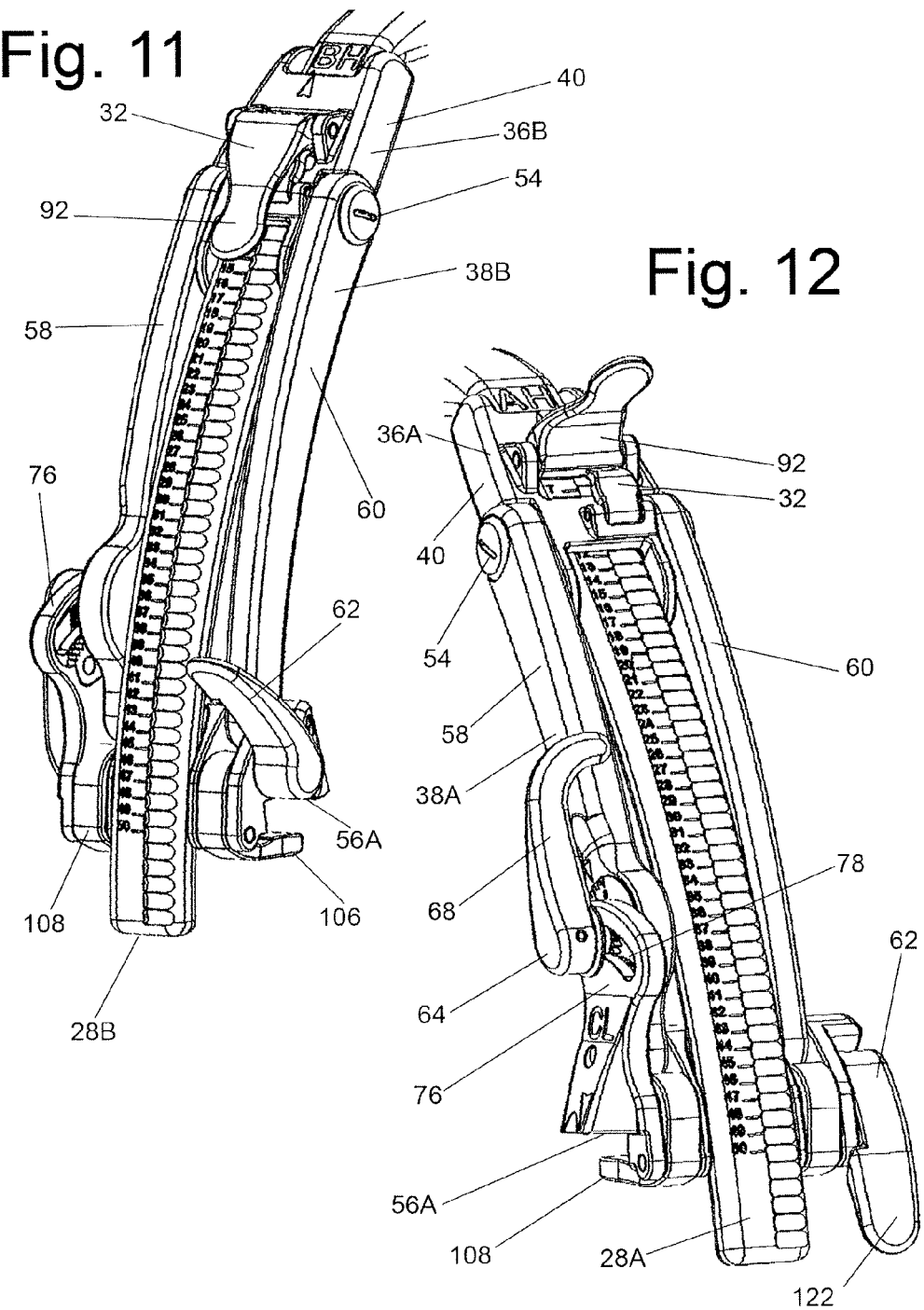

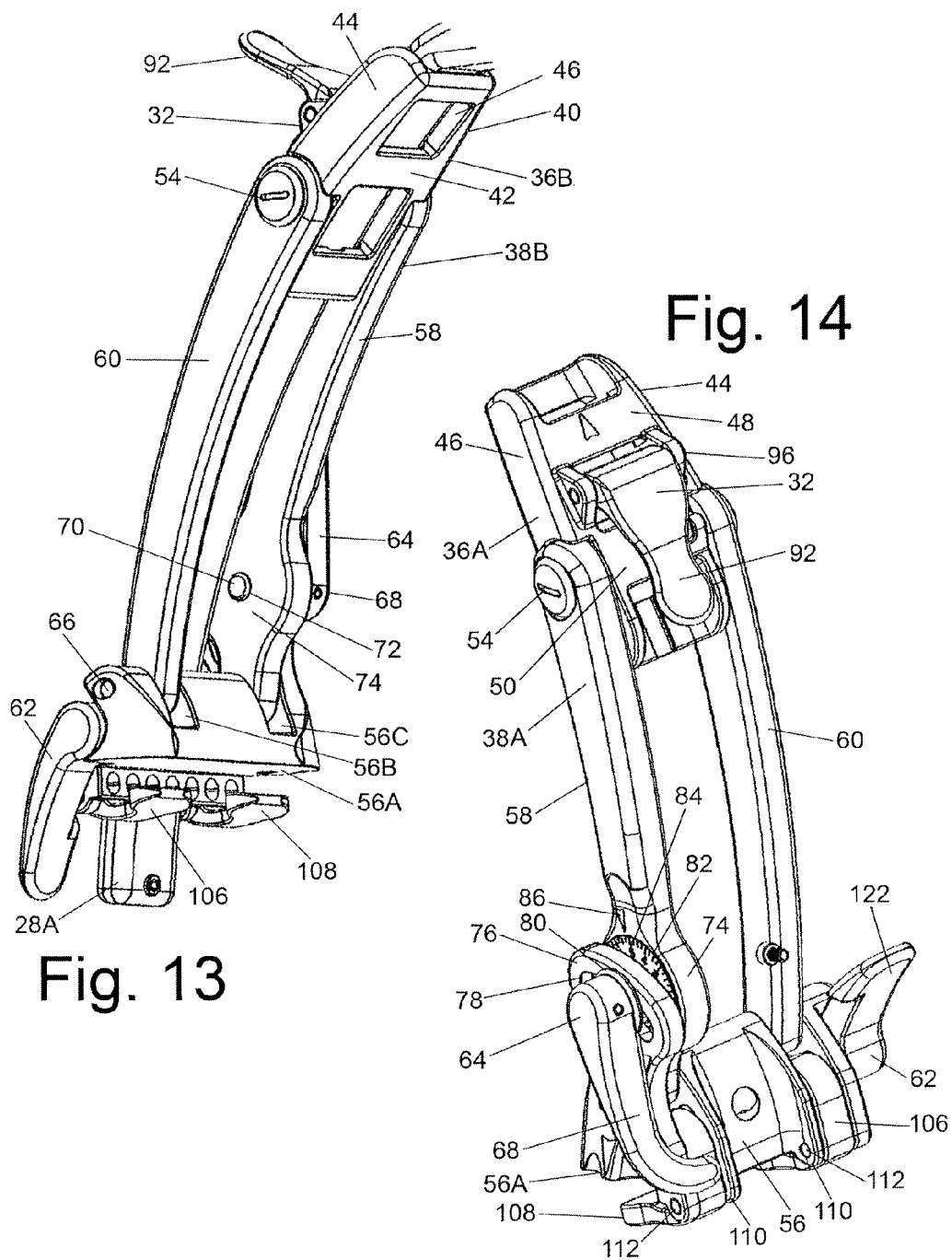

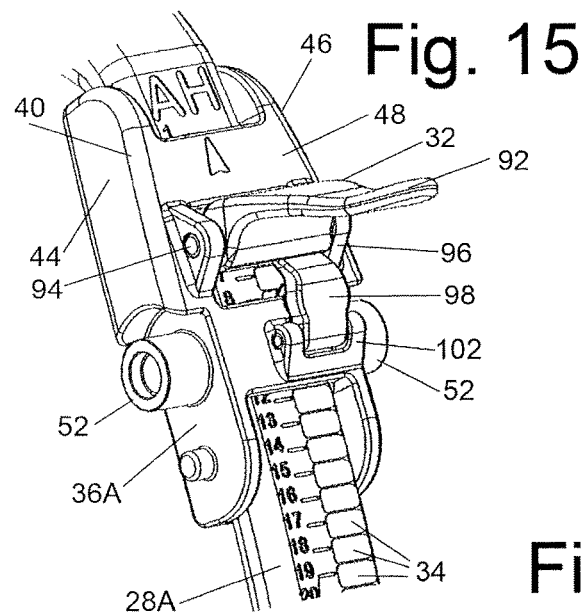
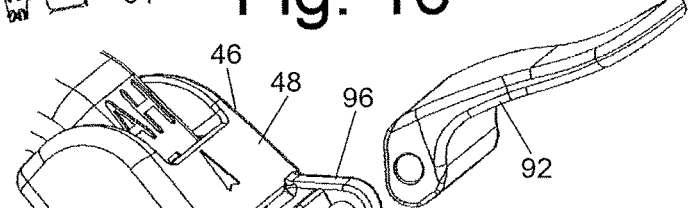
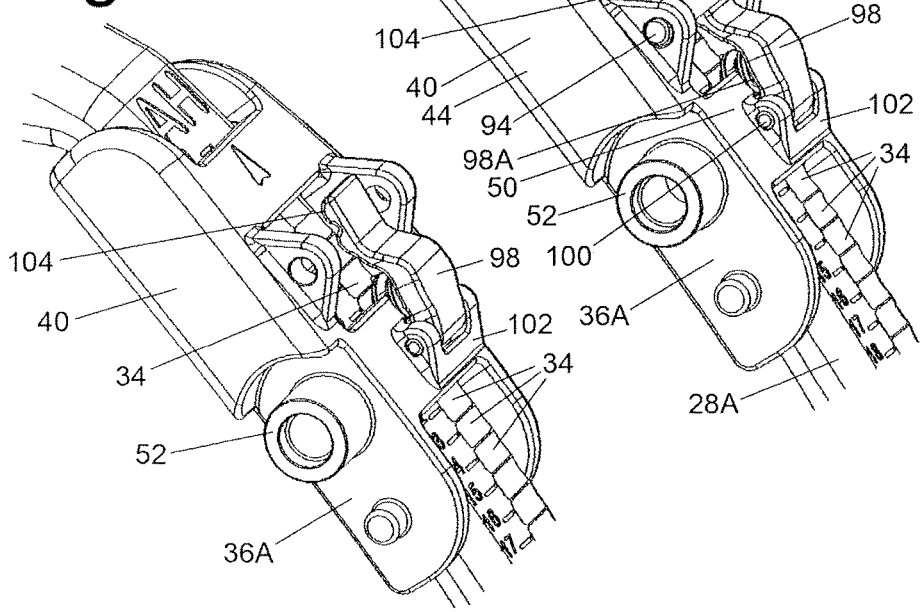

BRIDGE DEVICE FOR A PATIENT POSITIONING SYSTEM

CROSS-REFERENCE TO RELATED APPLICATIONS

This utility application claims the benefit under 35 U.S.C. § 119(e) of Provisional Application Ser. No. 61/917,666, filed on Dec. 18, 2013 entitled Bridge Device For A Patient Positioning System, whose entire disclosure is incorporated by reference herein and which is assigned to the same assignee as the subject invention.

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

This invention relates generally to holding devices and more particularly for bridge assemblies for holding positioning, fixation and associated devices on a radiation treatment couch or other patient support structure.

BACKGROUND OF THE INVENTION

Stereotactic Body Radiotherapy (SBRT) has gained wide acceptance for the treatment of cancer. In SBRT a patient is given repeated doses of radiation over an extended period of time. In order to ensure that the appropriate radiation dose is accurately delivered to the tumor each time that the patient is given a radiation treatment, various devices and systems are commercially available to hold or fix or hold in position the portion of the patient to which the radiation is to be directed. Such systems are sometimes referred to as patient positioning systems and serve to keep the patient as still as possible when the treatment beam is on. Patients undergoing SBRT typically are disposed on a treatment couch or table associated with a LINAC or other radiation therapy apparatus. Various couchtops and overlays are commercially available for disposition on the treatment couch, with the patient being disposed on the couchtop/overlay. As is known such support devices are disposed on top of the cradle, existing support frame and/or spine of a CT, simulator or LINAC. For SBRT applications it is a common practice to position and fix a portion of the patient so that repeated treatment can be given to the patient. To that end, some indexing system is provided for mounting and positioning various patient positioning and/or fixation devices on the couchtop or overlay at predetermined positions with respect to the couchtop/overlay. Examples of such patient positioning/fixation devices are head and neck positioning/fixation devices, breast and thorax positioning/fixation devices, and hip and pelvic region positioning/fixation devices. Many of such devices, as well as other miscellaneous positioning aids, e.g., cushions, wedges, etc., for use on the treatment couchtop/overlay are available from Civco Medical Solutions (hereinafter "CIVCO").

For example, CIVCO offers a BODY PRO-LOK™ system which aids in providing comfortable, total body immobilization for lengthy hypo-fractionation treatments, and is compatible with other treatment types, including Rapid Arc™, VMAT, IMRT, IGRT, SBRT, protons and more. That system includes, among other things, a carbon fiber platform, various types of bridges, and two-pin bars that allows Body Pro-Lok components to index to treatment couches from various vendors, such as Varian, Siemens, Elekta and Tomotherapy. The treatment couchtops/overlays available from CIVCO make use of an array of equidistantly spaced indexing points running down the side of the couchtop/overlay to which the two-pin LOK-BAR™ is configured to be connected at any of the indexing points. In particular, to index a particular positioning/fixation device to the couchtop or overlay the LOK-BAR™ is attached to the couchtop or overlay via any of the multiple indexing points. The particular patient positioning/fixation device is then mounted on the LOK-BAR™. By indexing the patient positioning/fixation device(s) to the same indexing points for every radiation treatment one can be assured of increased target accuracy and patient throughput.

While other manufacturers provide couchtops/overlays with indexing systems and positioning/fixation devices to be used with such indexing systems to perform a specific method of patient positioning and/or immobilization and there are specific devices designed for various niche approaches to SBRT, what had been missing is a general solution for immobilizing patients that is sufficiently versatile to have broad appeal to multiple centers doing SBRT.

In U.S. Pat. No. 8,146,599 (Wilson et al.), which is assigned to the same assignee as the subject invention, and whose disclosure is incorporated by reference herein, patient positioning systems are disclosed which are modular in design and provide an integrated solution that allows the user to tailor the positioning and immobilization methods to suit the patient, their LINAC (or other therapy apparatus) and their treatment plan. The systems disclosed in that patent make use of various components, such as a portable platform (referred to as a "patient support panel") and various devices for use on the patient support panel, so that when used patent comfort, setup time and patient transportation can be optimized. The patient support panel basically comprises a generally planar panel having a pair of side rails that enable full indexing of various components used during SBRT along its length. Among those components are modular multifunctional bridge devices that are arranged to be positioned anywhere along the length of the platform to be used to position/fix the patient or provide any other function desired during SBRT treatment. The multifunctional bridge devices are particularly significant in that they can be positioned where needed to provide various types of immobilization, hold instrumentation or enable stereotactic frames or other positioning and localization devices to be used.

While the bridge devices disclosed in the aforementioned patent and which are available from CIVCO are generally suitable for their intended purposes, they as well as other prior art bridge devices, leave something to be desired from various standpoints, such as the ability to achieve a wide range of adjustments, to shift laterally independent of the support platform and to enable each side of the bridge to be vertically adjustable independently to allow the angle of the central section of the bridge to vary relative to the surface of the support platform in the plane of the bridge. The subject invention addresses those needs.

All references cited and/or identified herein are specifically incorporated by reference herein.

SUMMARY OF THE INVENTION

In accordance with one aspect of the invention there is provided a bridge device for use with a patient positioning system. The patient positioning system includes a patient support panel, a right side rail and a left side rail, with the right and left side rails extending along and parallel to a central longitudinal axis of the patient support panel. The bridge device comprises a bridge member, a right side support assembly and a left side support assembly. The bridge member comprises an elongated right side section, an elongated left side section and an elongated central section connected between the right side section and the left side section. The right side section is configured to be releasably secured to the right side rail at various locations therealong by the right side support assembly, whereupon the right side section projects in an upward direction from the right side rail. The left side section is configured to be releasably secured to the left side rail at various locations therealong by the left side support assembly, whereupon the left side section projects in an upward direction from the left side rail with the central section extending over the patient support panel. The right side section is independently adjustable with respect to the right side support assembly and the left side section is independently adjustable with respect to the left side support assembly, whereupon the portion of the central section at the right side section can be disposed at any one of plural desired distances from the patient support panel and the portion of the central section at the left side section can be disposed at any one of plural desired distances from the patient support panel.

In accordance with one preferred aspect of the invention the central section of the bridge member is configured to be shifted laterally with respect to the central longitudinal axis of the patient support panel.

In accordance with another preferred aspect of the invention the right side support assembly comprises a right section that is configured to be pivoted about an axis parallel to the central longitudinal axis of the patient support panel to an angular orientation with respect to the patient support panel and the left side support assembly comprises a left section that is configured to be pivoted about an axis parallel to the central longitudinal axis of the patient support panel to an angular orientation with respect to the patient support panel.

In accordance with another preferred aspect of the invention the right side section of the bridge member includes a plurality of notches extending along at least a portion of the length thereof and the left side section of the bridge member includes a plurality of notches extending along at least a portion of the length thereof. In addition, the right support assembly comprises a clamp member configured to be releasably disposed in any one of the notches in the right side section of the bridge member to releasably secure the right side support assembly to the right side section of the bridge member. In a similar manner the left support assembly comprises a clamp member configured to be releasably disposed in any one of the notches in the left side section of the bridge member to releasably secure the left side support assembly to the left side section of the bridge member.

In accordance with another preferred aspect of the invention the right side section of the bridge member flares downward and away from the central section from the point at which the right side section is connected to the central section and the left side section of the bridge member flares downward and away from the central section from the point at which the left side section is connected to the central section.

In accordance with another preferred aspect of the invention the patient support panel includes an undersurface having an elongated recess extending parallel to the central longitudinal axis of the patient support panel adjacent the right side rail and an elongated recess extending parallel to that central longitudinal axis adjacent the left side rail. The clamp of the right support assembly is configured to releasably engage the elongated recess adjacent the right side rail and the clamp of the left support assembly is configured to releasably engage the elongated recess adjacent the left side rail.

In accordance with another preferred aspect of this invention a bridge device for use with a patient positioning system is provided. The patient positioning system includes a patient support panel, a right side rail and a left side rail, with the right and left side rails extending along and parallel to a central longitudinal axis of the patient support panel. The bridge device comprising a bridge member, a right side support assembly and a left side support assembly. The bridge member comprising an elongated right side section, an elongated left side section and an elongated central section connected between the right side section and the left side section. The right side section is configured to be releasably secured to the right side rail at various locations therealong by the right side support assembly, whereupon the right side section projects in an upward direction from the right side rail. The left side section is configured to be releasably secured to the left side rail at various locations therealong by the left side support assembly, whereupon the left side section projects in an upward direction from the left side rail. The central section extends over the patient support panel. The right side section is independently adjustable with respect to the right side support assembly and the left side section is independently adjustable with respect to the left side support assembly, whereupon the central section can be shifted laterally with respect to the central longitudinal axis of the patient support panel.

In accordance with another preferred aspect of this invention a bridge device for use with a patient positioning system is provided. The patient positioning system includes a patient support panel having a central longitudinal axis, a right side rail and a left side rail, with the right and left side rails extending along and parallel to the central longitudinal axis of the patient support panel. The bridge device comprises a bridge member, a right side support assembly and a left side support assembly. The bridge member comprises an elongated right side section, an elongated left side section and an elongated central section having a right side end connected to the right side section and a left side end connected to the left side section. The right side section is configured to be releasably secured to the right side rail at various locations therealong by the right side support assembly, whereupon the right side section projects in an upward direction from the right side rail. The left side section is configured to be releasably secured to the left side rail at various locations therealong by the left side support assembly, whereupon the left side section projects in an upward direction from the left side rail. The central section extends over the patient support panel. The right side section is independently adjustable with respect to the right side support assembly and the left side section is independently adjustable with respect to the left side support assembly, whereupon the distance of the right side end of the central section to the patient support panel can be adjusted as desired and the distance of the left side end of the central section to the patient support panel can be adjusted as desired.

In accordance with another preferred aspect of this invention a bridge device for use with a patient positioning system is provided. The patient positioning system includes a patient support panel having a central longitudinal axis, a right side rail and a left side rail, with the right and left side rails extending along and parallel to the central longitudinal axis of the patient support panel. The bridge device comprises a bridge member, a right side support assembly and a left side support assembly. The bridge member comprises an elongated right side section, an elongated left side section and an elongated central section connected between the right side section and the left side section. The right side section is configured to be releasably secured to the right side rail at various locations therealong by the right side support assembly, whereupon the right side section projects in an upward direction from the right side rail. The left side section is configured to be releasably secured to the left side rail at various locations therealong by the left side support assembly, whereupon the left side section projects in an upward direction from the left side rail. The central section extends over the patient support panel whereupon an area having a height and a width is created over the patient support panel between the bridge member and the right and left side support sections. The right side section is independently adjustable with respect to the right side support assembly and the left side section is independently adjustable with respect to the left side support assembly, whereupon the width and height of the area can be adjusted as desired.

DESCRIPTION OF THE DRAWING

FIG. 3 is a view similar to FIG. 2, slightly reduced in size, and showing the bridge device of FIG. 1 with the bridge member in its highest or extended position wherein the bridge member is centered over the patient support panel;

FIG. 4 is a view similar to FIG. 3, but showing the bridge device of FIG. 1 with the bridge member in one asymmetrical height position, i.e., one side of the bridge member being disposed closer to the patient support panel than the other side of the bridge member, with the bridge member being centered over the patient support panel;

FIG. 5 is a view similar to FIG. 4, but showing the bridge device of FIG. 1 with the bridge member in one laterally shifted position, i.e., one side of the bridge member being disposed closer to one side of the patient support panel than the other side of the bridge member so that the bridge member is not centered over the patient support panel;

FIG. 6 is an isometric view of the bridge member of the bridge device shown in FIGS. 1-5;

FIG. 6A is an enlarged isometric view of the portion of the bridge member shown within the circle designated 6A in FIG. 6;

FIG. 9 is an enlarged side elevation view taken from the left side of the bridge device shown in FIG. 1, with the left side of the bridge member being shown in its locked state;

FIG. 10 is an enlarged side elevation view taken from the right side of the bridge device shown in FIG. 1, with the right side of the bridge member being shown in its unlocked state;

FIG. 11 is an enlarged isometric view of the left side support assembly of the bridge device shown in FIG. 2, with the left side of the bridge member being shown in its locked state;

FIG. 12 is an enlarged isometric view of the right side support assembly of the bridge device shown in FIG. 2, with the right side of the bridge member being shown in its unlocked state;

FIG. 13 is an isometric view of the left side support assembly shown in FIG. 11, except that the left side support assembly is shown in its unlocked state and taken from a different angle so that the underside of the left side support assembly can be seen;

FIG. 14 is an isometric view of the right side support assembly shown in FIG. 12, except that the right side support assembly is shown in its locked state and without the bridge member being shown;

FIG. 15 is an enlarged isometric view of a portion, i.e., the upper section, of the unlocked right side support assembly shown in FIG. 12;

FIG. 16 is a partially exploded isometric view of the portion of the unlocked right side support assembly shown in FIG. 15;

FIG. 17 is an isometric view of the portion of the unlocked right side support assembly shown in FIG. 15, with some portions thereof being removed for clarity, to show the releasable locking of the rights side section of the bridge member to the upper section of the right side support assembly;

DETAILED DESCRIPTION OF THE PREFERRED EMBODIMENT

Figure 1:
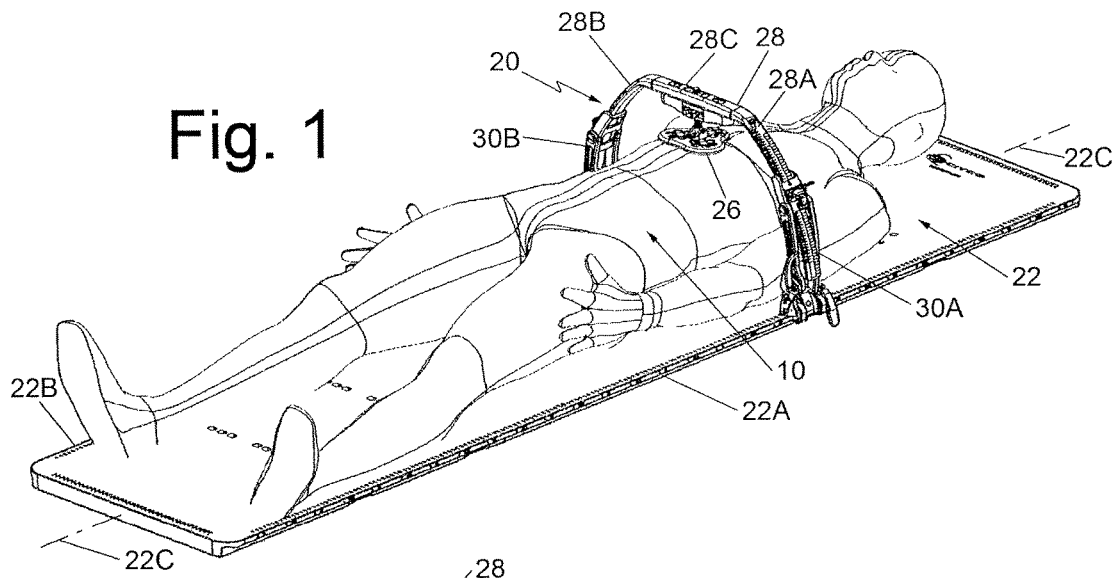
FIG. 1 is an isometric view of one exemplary embodiment of a bridge device having a bridge member constructed in accordance with this invention shown in one exemplary use mounted on an exemplary patient support panel to fix a portion of the patient in a desired position.

Referring now to the various figures of the drawing wherein like reference characters refer to like parts, there is shown in FIG. 1 a bridge device 20 constructed in accordance with one exemplary embodiment of this invention. The bridge device 20 is shown mounted on an exemplary patient support panel 22 of a patient positioning system. The patient support panel 22 is arranged to be used on a convention LINAC couchtop or table (not shown) or any other radiation producing apparatus having a couchtop or table to repeatedly position/fix any portion of the body of a patient at any desired positions for SBRT or any other procedure requiring repeated immobilization of that portion of patient's body. The patient support panel 22 can be of any suitable type that is commercially available, such as those sold by CIVCO, or other manufacturers. In accordance with one preferred embodiment of the invention the patient support panel is constructed in accordance with the teaching of the aforementioned Wilson et al. patent. Thus, the patient support panel 22 can be a removable device to serves as a means for providing mounting rails in a CT or LINAC environment. It could also be in the form of a universal couch top that may be permanently attached to a table or pedestal.

As best seen in FIGS. 1-5 the exemplary patient support panel 22 basically comprises a generally planar member which is of sufficient size to support an adult patient 10 in a prone position thereon. The patient support panel 22 has a pair of longitudinally extending side rails 22A and 22B and a central longitudinal axis 22C. The side rails enable full indexing of various components, such as but not limited to the bridge device 20, used during SBRT along the length of the patient support panel. In particular, the longitudinal side edges of the patient support panel 22 are of a bulbous form in cross section to define the side rails. As best seen in FIG. 5, the undersurface of the support panel immediately adjacent the side rail 22A is in the form of an arcuate recess or groove 22D, while the undersurface of the support panel immediately adjacent the side rail 22B is in the form of an arcuate recess or groove 22E. Each groove 22D and 22E extends the length of the patient support panel and parallel to the central longitudinal axis 22C. The grooves 22D and 22E are arranged to receive a portion of a respective clamp (to be described later) of the bridge device 20 to enable the bridge device to be located at any desired longitudinal position along the length of the patient support panel. If desired, each side rail can include a plurality of equidistantly spaced (i.e., 7 cm), indexing buttons, apertures or holes that are aligned transversely in pairs so that a two-pin registration or locking bar (not shown), like the two-pin LOK-BAR™, can be mounted on the patient support panel between any pair of buttons, apertures, etc., with the buttons/apertures providing incremental steps for positional indexing of the bridge member.

The bridge assembly 20 is arranged to mount or support a multitude of positioning/fixation devices on it and for it to be mounted on the patient support panel (via the side rails 22A and 22B) at various positions along the length of the patient positioning panel and not merely at any discrete indexing points established by the pairs of apertures in the side rails if the patient support panel includes such indexing apertures. One exemplary positioning device is a chest plate 26 (shown in FIG. 1) which is releasably mounted on a central portion of a bridge member (to be described later).

Figure 2:
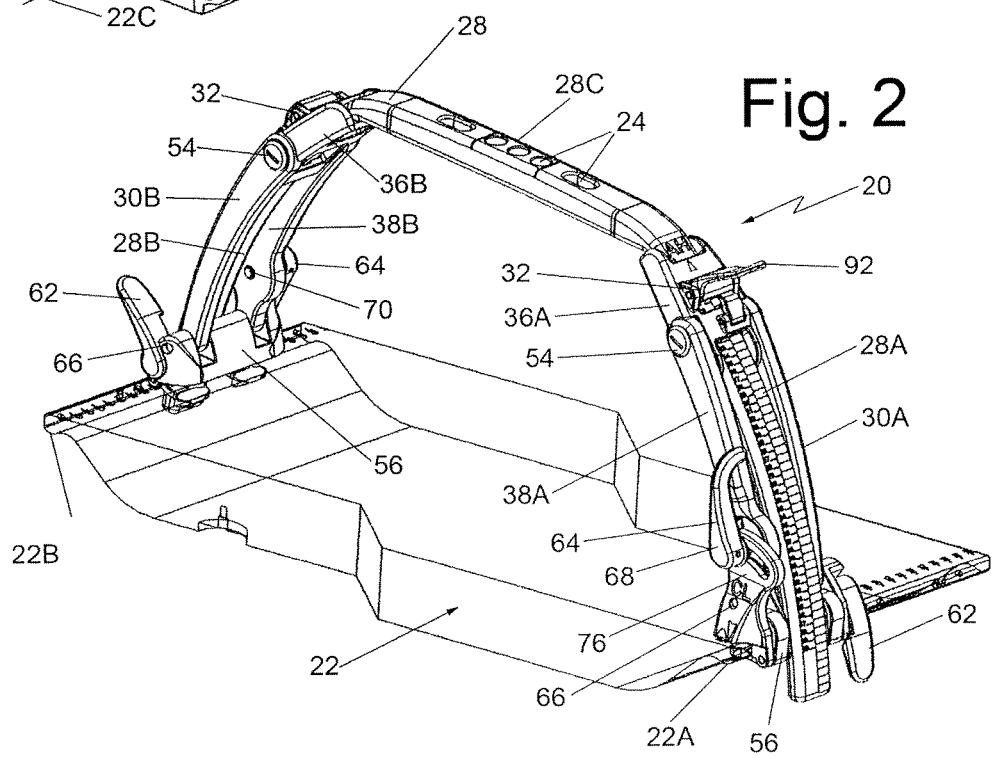
FIG. 2 is an enlarged isometric view of the bridge device of FIG. 1 with the bridge member shown in its lowest or retracted position wherein the bridge member is centered over the patient support panel.
Figure 7:
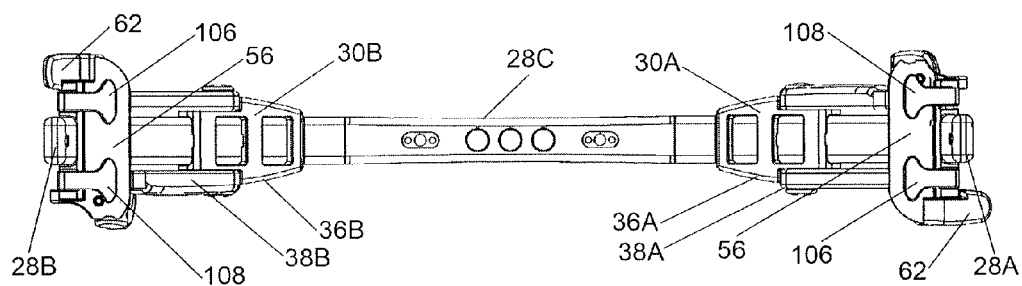
FIG. 7 is a bottom plan view of the bridge device of FIGS. 1-5 with the patient support panel removed.
Figure 8:
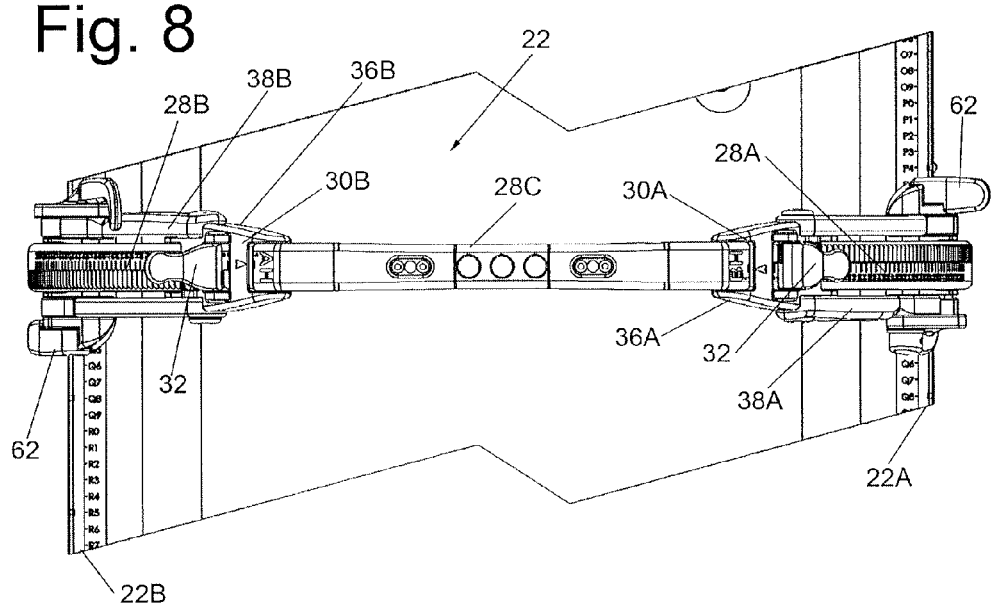
FIG. 8 is a top plan view of the bridge device of FIGS. 1-5.

The bridge assembly is best seen in FIGS. 2-4 and basically comprises a bridge member 28, a right side support assembly 30A and a left side support assembly 30B. The bridge member 28 is best seen in FIG. 6 and is substantially rigid member formed of any suitable material like those used in prior art bridges for SBRT and other similar applications. The bridge member 28 comprises an elongated and arcuate right side section 28A, an elongated and arcuate left side section 28B and an elongated and generally linear central section 28C connected between the right side section and said left side section. The right side section 28A projects downward and outward from the right side of the central section 28C and the left side section 28B projects downward and outward from the left side of the central section 28C. Thus, the two side sections 28A and 28B can be said to flare outward and downward from their respective sides of the central section. While the right and left side sections are preferably arcuate, it is contemplated that they may, if desired, be linear providing that they flare outward and downward from the central section, as will be appreciated from the discussion following later. The central section includes plural, e.g., 3, holes 24A which are centrally located and plural, e.g., 2, slots 24B located outside the central holes 24A, all of which extending through the central section. The holes 24A serve to mount a fixation component, e.g., the chest plate 26, onto the central section of the bridge member 28, e.g., they provide clearance for the respiratory restriction device's lead screw. Moreover, plural push pins (not shown) are provided to serve as additional means of securing fixation components to the bridge member. To that end, the slots 24B in the central section provide the mounting geometry for the base of each push pin and clearance for the push pins.

Providing side sections 28A and 28B, which are angled with respect to the central section 28C as just described, effectively increases the length of the side sections and hence the range of travel with respect to respective upper sections (to be described later) of the side support assemblies 30A and 30B, for any given elevation of the central section 28C above the patient support panel 22. Thus, the bridge device 20 of this invention permits a greater range of adjustment than prior art bridges. In particular, the angled side sections 28A and 28B enable one to achieve a maximum height of the central section 28C of the bridge member with respect to the patient support surface 22, such as shown in FIG. 3, while enabling that section to be set at the lowest position with respect to the patient support panel, such as shown in FIG. 2, without the free ends of the side sections 28A and 28B extending substantially below the patient support panel 22. Moreover, the angling inward of the side sections from their free distal end to the portion at which they merge with the central section enables the bridge device 28 to be readily accommodated within a circular area, such as the bore of the treatment apparatus, e.g., the LINAC, MRI, CT scan apparatus, or the gantry which encircles the patient during the treatment. Making the side sections arcuate provides even greater space within the bounds of the bridge device for the patient and can closely fit within the bore of the treatment apparatus when the bridge is set in its maximum extended position.

In accordance with one exemplary embodiment of the invention, the bridge member 28 is an integral member, but is preferably formed of three separate components fixedly secured together. In particular, the right side section is a separate member that is fixedly secured to the right side of the central section by an internal pin (not shown) and the left side section is a separate member that is fixedly secured to the left side of the central section by an internal pin (not shown). If desired, the bridge member 28 can be formed as an integral unit, e.g., molded as a one-piece construction.

The right side section 28A of the bridge member 28 is arranged to be releasably secured to the right side rail 22A of the patient support panel 22 at various locations therealong by the right side support assembly 30A, whereupon the right side section projects in an upward direction from the right side rail. Similarly, the left side section 28B of the bridge member 28 is arranged to be releasably secured to the left side rail 22B at various locations therealong by the left side support assembly 30B, whereupon left side section projects in an upward direction from the left side rail. The central section 28C bridges the patient support panel 22 between the right and left side support assemblies.

One of the significant aspects of bridge device 20 is that the right side section of the bridge member 28 is independently adjustable in position with respect to the right side support assembly 30A, and the left side section of the bridge member is independently adjustable with respect to the left side support assembly 30B, whereupon the portion of the central section 28C at the right side section can be disposed at any one of various desired distances from the top surface of the patient support panel and the portion of the central section at left side section can be independently disposed at any one of various desired distances from the top surface of the patient support panel. The details of the construction of the bridge member 28 and the side support assemblies 30A and 30B to accomplish that function will be described in detail later. Suffice for now to state the side support assembly 30A includes a releasably securable connector or lock assembly 32 (to be described in detail later) arranged to releasably engage a portion of the side section 28A of the bridge member at any longitudinal position therealong. In a similar manner, the side support assembly 30B includes an identical releasably securable connector assembly 32 arranged to releasably engage a portion of the side section 28B of the bridge member at any longitudinal position therealong.

As best seen in FIGS. 6 and 6A, the outer surface of the side section 28A includes a series of notches or grooves 34 extending parallel to the longitudinal central axis 22C. In a similar manner, the outer surface of the side section 28B includes a series of notches or grooves 34 extending parallel to the longitudinal central axis 22C. The releasably securable connector assembly 32 of each side support assembly is arranged to engage any one of the notches of the associated side section of the bridge member to establish the position of the bridge section with respect to the patient support panel. For example, FIG. 2 shows the bridge device 20 in its most retracted or compact state, wherein an engagement component (to be described later) of each of the respective releasably securable connector 32 is aligned with the uppermost notch 34 in the two side sections 28A and 28B. In this state the central section 28C of the bridge member 28 is parallel to the top surface of the patient support panel, is centered thereover, and each side of the central section 28 is at the same and closest distance from that top surface. In FIG. 3 the bridge device 20 is shown in its most extended or expanded state, wherein the engagement component of each of the respective releasably securable connector is aligned with the lowermost notch 34 in the two side sections 28A and 28B. In this state the central section 28C of the bridge member is parallel to the patient support surface, is centered thereover, and each end of the central section is at the same and furthest distance from the top surface of the patient support panel. In FIG. 4, the bridge device is shown in one of many exemplary asymmetrical states, i.e., the right side of the central section 28C of the bridge member 28 is located at a lesser distance from the top surface of the patient support panel than the left side of the central section 28C, but the central section is still centered over the top surface of the patient support panel. Thus, in this exemplary configuration the engagement component of the releasably securable connector assembly of the side support assembly 30A is aligned with a notch 34 of the side section 28A closer to the central section 28C than the notch 34 of the side section 28B which is in alignment with engagement component of the releasably securable connector assembly of the side support assembly 30B.

In FIG. 5, the bridge device 20 is shown in another of many exemplary states wherein the central section 28C of its bridge member 28 is not centered over the patient support panel. Rather it is shifted laterally, in this case to the right.

In order to enable the bridge device 20 to assume the various configurations shown in FIGS. 2-5, as well as any other configuration that the device is capable of assuming, the side support assemblies 30A and 30B each include two sections which are enabled to pivot about respective axes parallel to the central longitudinal axis 22C of the patient support panel 22. In particular, the side support assembly 30A includes an upper section 36A and a lower section 38A. Similarly, the side support assembly 30B includes an upper section 36B and a lower section 38B. The releasably securable connector 32 of the side support assembly 30A is mounted on upper section 36A thereof, while the releasably securable connector 32 of the side support assembly 30B is mounted on upper section 36B thereof.

Both side support assemblies 30A and 30B are of identical construction. Thus, in the interest of brevity the details of only one of those assemblies, i.e., 30A, will be described in detail in the discussion to follow. To that end the upper section 36A of the assembly 30A is best seen in FIGS. 13 and 15-17 and basically comprises a sleeve-like body or frame 40 having a bottom wall 42, and opposed pair of sidewalls 44 and 46 and two spaced-apart top walls 48 and 50. The walls together define a channel between them which is arranged to receive the side section 28A of the bridge member 28 as best seen in FIGS. 15-17. Each of the sidewalls 44 and 46 includes a circular tubular projection 52 extending outward perpendicularly from its associated sidewall. The tubular projections are axially aligned and serve to receive a screw 54 (FIG. 13) to pivotably connect the upper section 36A to the lower section 38A Thus the longitudinal axis of the screw 54, which is parallel to the central longitudinal axis 22C of the patient support panel, serves as the axis enabling the upper section 36A to pivot with respect to the lower section 38A.

Figure 18:
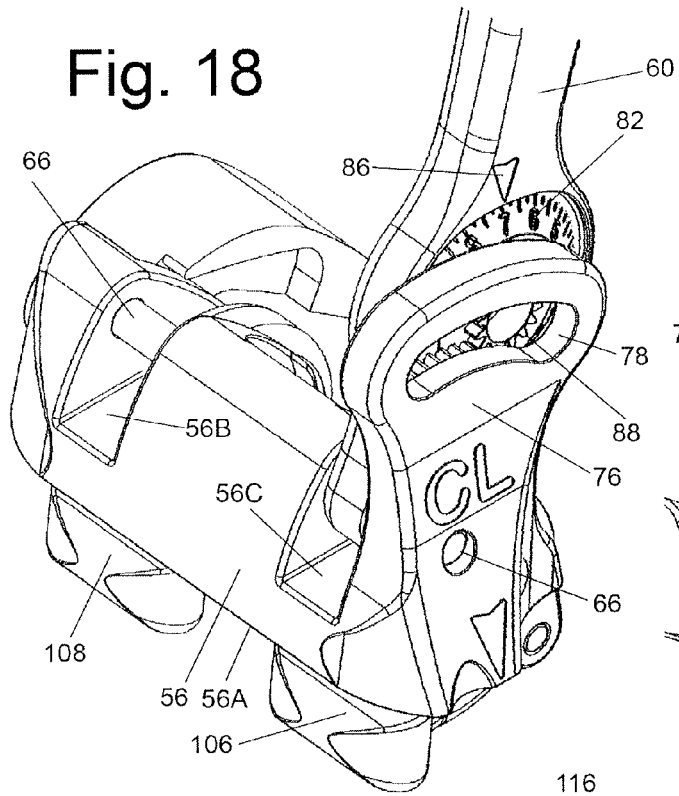
FIG. 18 is an enlarged isometric view of a portion of the right side support assembly including its base and the clamp assembly for releasably securing the right side support assembly to the right rail of the patient support panel.

As best seen in FIGS. 13, 14 and 18 the lower section 38A basically comprises a base 56, a pair of elongated struts or links 58 and 60, a rail clamp assembly 62, and an orientation clamp or lock assembly 64. The base 56 includes an undersurface 56A, and two slots 56B and 56C. The slots 56B and 56C are arranged to receive the lower end of the links 60 and 58, respectively. The base also includes a flange 76 projecting upward from one side of it. The flange 76 forms one side of the slot 56C. A pivot pin 66 extends through the base (including flange 76), the slots and through aligned holes (not shown) in the lower portions of links 58 and 60 to pivotably connect those links to the base. Thus, the longitudinal axis of the pin 66, which is parallel to the longitudinal central axis 22C, serves as the axis enabling the lower section 38A to pivot with respect to the base 56. The base 56 is arranged to be fixedly secured to the side rail 22A by the rail clamp assembly 62 (whose details will be described later). The upper portion of the link 58 includes a hole (not shown) through which the tubular projection 52 of the sidewall 44 extends, while the upper portion of the link 60 includes a hole (not shown) which is axially aligned with the hole in the upper end of the link 58 through which the tubular projection 52 of the sidewall 46 extends. The screw 54 extends through the hollow interiors of the aligned projections 52 in the links 58 and 60 to pivotably connect the upper section 36A to the lower section 38A as described above.

As should be appreciated by those skilled in the art the positioning of the side sections 28A and 28B of the bridge member 28 with respect to the upper sections 36A and 36B, respectively, of the side support assemblies 30A and 30B to establish the size and orientation of the bridge member, such as shown in the examples of FIGS. 2-5, will result in automatic pivoting of the various sections of those side support assemblies. In particular, the upper sections 36A and 36B, will automatically pivot about their respective pivot axes (the axes of their associated screws 54) with respect to the lower sections 38A and 38B, respectively, and lower sections 38A and 38B will automatically pivot about their respective axes (the axes of their associated pins 66) with respect to the base 56 of the side support sections 30A and 30B, respectively, to the orientations shown in those figures.

In order to lock the side assemblies in those orientations the heretofore mentioned orientation lock assemblies 64 are utilized. The orientation lock assembly 64 of the side support assembly 30A is of identical construction to the orientation lock assembly 64 of the side support assembly 30B. Thus, in the interest of brevity the details of only the orientation lock assembly 64 of the side support assembly 30A will be discussed.

As can be seen the orientation lock assembly 64 basically comprises a handle 68 from which a threaded screw 70 (FIG. 13) projects the distal end of the screw 70 is threadedly engaged in a threaded hole 72 in an enlarged area portion 74 of the link 58 of the lower section 38A. As mentioned earlier the base 56 of the side support assembly 30A includes a flange 76 projecting upward therefrom. The flange includes an arcuate slot 78 through which the screw 70 of the handle 68 passes. A washer 80 is provided between the handle 68 and the flange 76. As should be appreciated by those skilled in the art pivoting the handle 68 downward will cause the screw to tighten to lock the lower section 38A of the side support assembly 30A in its desired orientation, while pivoting the handle upward will loosen the screw and thus free the lower section so that it can be moved into any desired orientation about the axis of the pivot pin 66.

Figure 19:
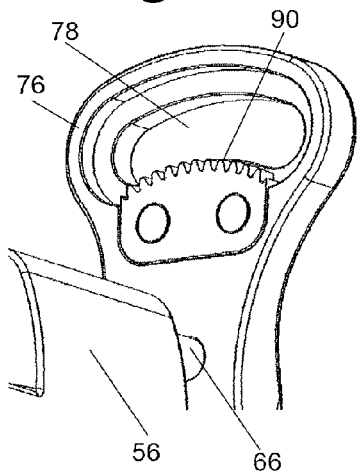
FIG. 19 is an enlarged isometric view of a portion of the base of the right side support assembly.

As can be seen in FIGS. 14 and 18 the lower section 38A includes a circular disk 82 having a series spaced-apart indicia lines and associated numbers 84 extending about the periphery on the outer surface of the disk. The disk is located within a correspondingly shaped circular recess in the outer surface of the enlarged portion 74 of the link 58. A pointer 86 is located on the outer surface of the link 58 just above the disk 82. The central portion of the disk includes a gear 88 (FIG. 18) surrounding the passageway through which the screw 70 of the handle 68 extends. The gear 88 is arranged to roll along a slightly arcuate toothed rack 90 (FIG. 19) on the inner surface of the flange 76 of the base 56 immediately below the arcuate slot 78. Thus, upon pivoting of the lower section 38A of the right support assembly 30A, the pointer 86 will point to the indicia 84 on the disk 82 (which will have rotated with the pivoting of the lower section 38A), thereby indicating the angular position of the lower section 38A of the right support assembly 30A. Twisting of the handle 68 downward (in the clockwise direction of FIG. 14) will lock the lower section of the right side support assembly in that orientation, whereas pivoting of the handle in the upward or counterclockwise direction will release or free the lower section of the right side support assembly so that the lower section 38A can be pivoted into any desired orientation.

Turning now to FIGS. 15-17, the details of the releasably securable connector assemblies 32 for locking the side sections of the bridge member to the upper sections of the side support assemblies will now be described. The releasably securable connector assembly 32 of the side support assembly 30A is of identical construction to the releasably securable connector assembly 32 of the side support assembly 30B. Thus, in the interest of brevity the details of only the releasably securable connector assembly 32 of the right side support assembly 30A will be discussed. As can be seen best in FIG. 15 the upper section 36A of the right support assembly 30A includes a latch lever 92 pivotably connected via a pin 94 mounted on a yoke 96 at the top wall 48 of the sleeve-like body 40. A cam finger 98 is pivotably connected via a pin 100 in a yoke 102 on at the top wall 50. As best seen in FIGS. 16 and 17, the free end of the cam finger 98 is biased by a compression spring 98A located between it and the top wall 50. The cam finger includes an engagement surface 104 on its underside which is matingly shaped and arranged to be received within any of the grooves 34 in the side section 28A of the bridge member 28 against the bias of the spring 98A. The latch lever 92 includes a cam surface that is arranged to engage a cooperating cam surface on the top surface of the cam finger 98 when the latch lever 92 is pivoted downward (in the clockwise direction shown in FIG. 15) to engage the top surface of the cam finger to pivot it downward and to lock the cam finger and the latch lever in the downward state like shown in FIG. 14. In this state the engagement surface 104 enters into the aligned groove 34 and is releasably locked in place therein until the latch lever is released. Accordingly, this action locks the upper section 36A of the right side support assembly 30A to the side section 28A of the bridge member 28.

Figure 20:
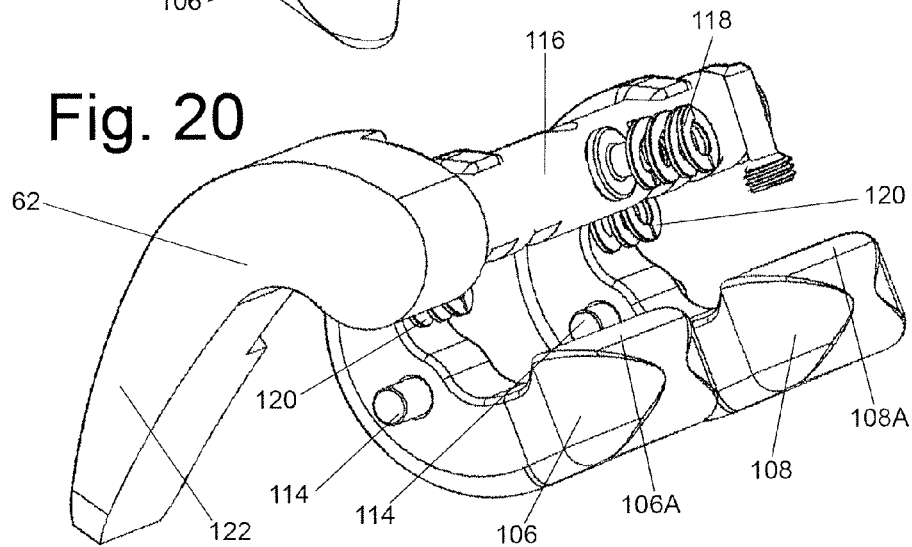
FIG. 20 is an enlarged isometric view of a portion of the clamp assembly of the right side support assembly for releasably securing the right side support assembly to the right side rail of the patient support panel.
Figure 21:
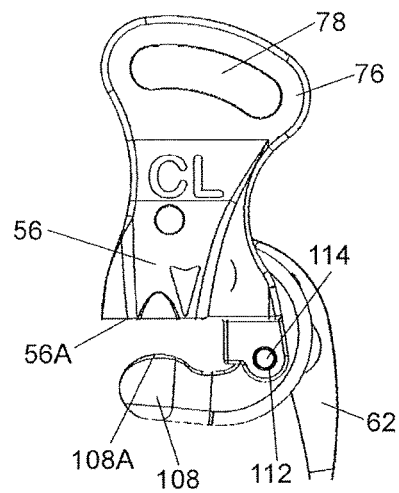
FIG. 21 is a side elevation view of the portion of the right side support assembly shown in FIG. 18.

Turning now to FIGS. 13, 18, 20 and 21 the details of the rail clamp assemblies 62 for locking the right side support assembly 30A at any longitudinal position along the side rails 22A will now be described. It must be pointed out at this juncture that the rail clamp assembly 62 of both side support assemblies 30A and 30B are of identical construction. Thus, in the interest of brevity the details of only one of those rail clamp assemblies, i.e., the rail clamp assembly of right side support assembly 30A, will be described in detail in the discussion to follow. To that end, that rail clamp assembly basically comprises a pair of generally C-shaped clamp members 106 and 108 (FIG. 21), each of which is pivotably mounted in via flanges 110 (FIG. 14 projecting downward from the base 56. Each flange includes a hole 112 for receipt of a pivot pin 114 of a respective C-shaped clamp member to pivotably mount the C-shaped clamp member on the base 56. As best seen in FIG. 20, the upper end of each C-shaped clamp member is mounted in a respective slot in a rotatable shaft 116. The shaft 116 extends through the interior of the base 56 and is biased by helical compression springs 118 and 120. A handle or lever 122 is connected to one end of the shaft 116. The top surface 106A of the bottom portion of the C-shaped clamp member 106 is disposed opposite the planar undersurface 56A of the base 56. In a similar manner the top surface 108A of the bottom portion of the C-shaped clamp member 108 is disposed opposite the planar undersurface 56A of the base 56. The undersurface 56A is arranged to abut the top surface of the patient support panel at the side rail 22A. The top surface 106A of the C-shaped clamp member 106 and the top surface 108A of the C-shaped clamp member 108 are arranged to be disposed and engage the recess or groove 22D on the undersurface of the patient support panel 22 adjacent the side rail 22A. Thus, when the handle or lever is rotated against the bias of the springs to the lock position it causes the C-shaped members to pivot about the axis of the pins 114 to a closed position which causes the upper surfaces 106A and 108A of the C-shaped members to engage the groove 22D and thereby tightly sandwich the patient support panel at the location of the groove between those surfaces and the undersurface of the base. The C-shaped clamp members include cam surfaces which cooperate with cam surfaces on the base to releasably lock them in the closed position against the bias of the springs. This action releasably locks the base to the side rail at whatever longitudinal position along the side rail it happens to be. Rotating the handle or lever 122 in the opposite direction releases the C-shaped clamp members from the side rail to which that base member is secured.

In use, when the patient is in position on the top surface of the patient support panel 22, like shown in FIG. 1, each of the two side support assemblies 30A and 30B of the bridge device 20 can be placed on the patient support panel by moving each latch lever or handle 122 of its rail clamp assembly to the position wherein the two C-shaped clamp members are open, like shown in FIG. 14. The two side support assemblies can then be placed on their respective side rails of the patient support panel at the desired longitudinal position along the length of the patient support panel and not merely at the discrete indexing points established by the pairs of apertures (if any) in the side rails.

Once the side support assemblies 30A and 30B are at their desired position on the side rails, their releasably securable connector assemblies 32 are then moved to their open state, if they are not already in that state. Thus, the free end of the side section 28A of the bridge member 28 can be threaded through the sleeve-like body 40 of the upper section 36A of the side support assembly 30A, without interference from its releasably securable connector assembly 32. In a similar manner the free end of the side section 28B of the bridge member 28 can be threaded through the sleeve-like frame 40 of the upper section 36B of the side support assembly 30B, without interference from its releasably securable connector assembly 32. The height and lateral position of the central section 28C of the bridge member 28 from the patient support panel can then be established. This is accomplished by sliding the side section 28A of the bridge member 28 with respect to the upper section 36A until the desired notch 34 in that side section is aligned with the engagement surface 104 of the associated releasably securable connector assembly 34. Then the latch lever 92 of the releasably securable connector assembly 32 can be rotated downward to force the engagement surface into the aligned groove and thereby releasably secure the upper section of the side support assemblies 36A to the side sections 28A of the bridge member 28. The side section 28B can be similarly adjusted with respect to the upper section 36B of the side support assembly 30B. The position at which the two upper sections of the side support assemblies are releasably secured to their respect side sections of the bridge member 28 are indicated by indicia provided on the outer surface of each of those side sections as shown clearly in FIGS. 9 and 10. While the indicia are shown in this exemplary embodiment as successive numbers, e.g. 1-50, they can take any form, e.g., they can be letters, colors, etc.

As should be appreciated by those skilled in the art the releasable securement of the two side sections 28A and 28B to their respective upper sections 36A and 36B will automatically cause the upper sections 36A and 36B to rotate about their respective pivot axes (i.e., the longitudinal axes of their respective screws 54). Once that has been accomplished the lower sections 38A and 38B of the side support assemblies 30A and 30B, respectively, can be pivoted about the pivot axes 66 of their respective bases 56 to establish the lateral position of the central section 28C of the bridge member. The pivoting of the lower sections with respect to their bases will also result in the associated pivoting of their upper sections to accommodate the pivoting of the lower sections. Once the central section of the bridge member is at its desired height and lateral position orientation, the orientation clamp assemblies 64 can be locked in place by the pivoting of their handles 68 downward.

It should be pointed out at this juncture that the sequence for mounting and adjusting the bridge device 20 need not be accomplished only in the manner as described above. Thus, the bridge device 20 may be preassembled, i.e., the bridge member 28 secured to the side support assemblies 30A and 30B and that entire unit then mounted on the patient support panel 22 at the desired longitudinal position, height and lateral displacement. It should also be noted that any of a number of patient engagement components may be releasably mounted to the central section 28C of the bridge member. To that end, the central section of the bridge member includes plural openings to which such components can be connected.

Figure 22:
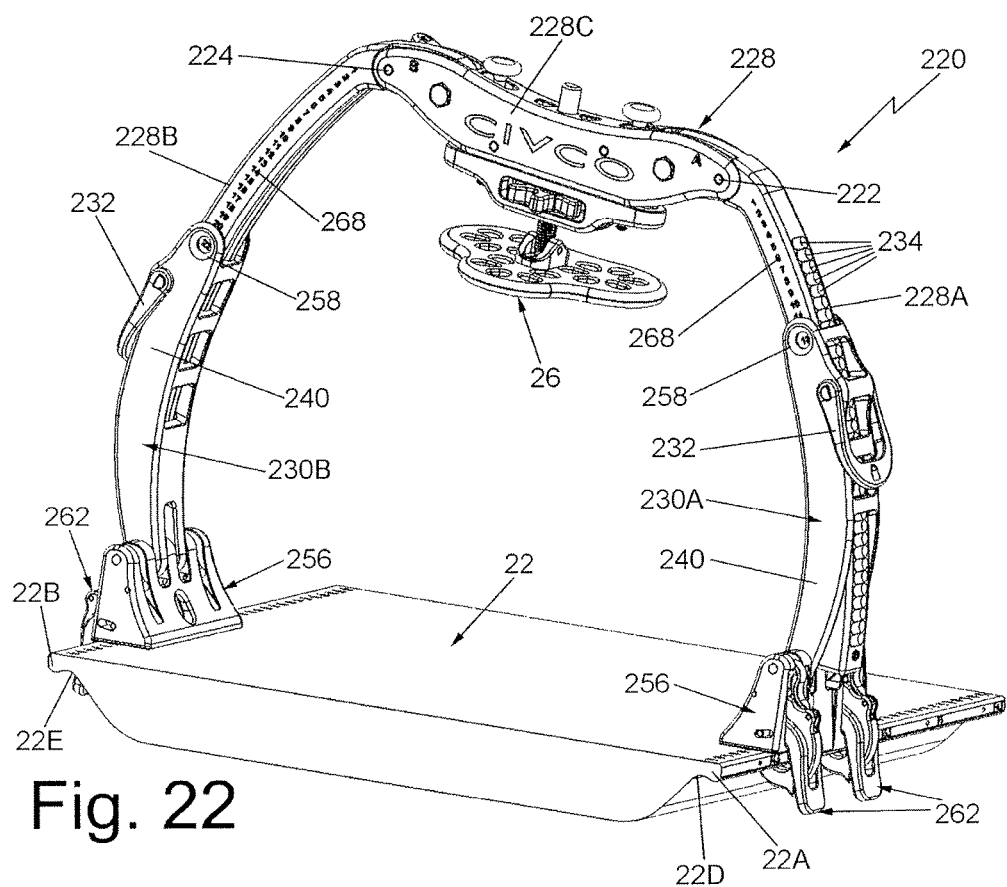
FIG. 22 is an isometric view, similar to FIG. 2, but showing another and more preferred exemplary embodiment of a bridge device having a bridge member constructed in accordance with this invention, with the bridge device being shown mounted on an exemplary patient support panel and wherein the bridge member is in an exemplary asymmetrical orientation over the patient support panel.
Figure 23:
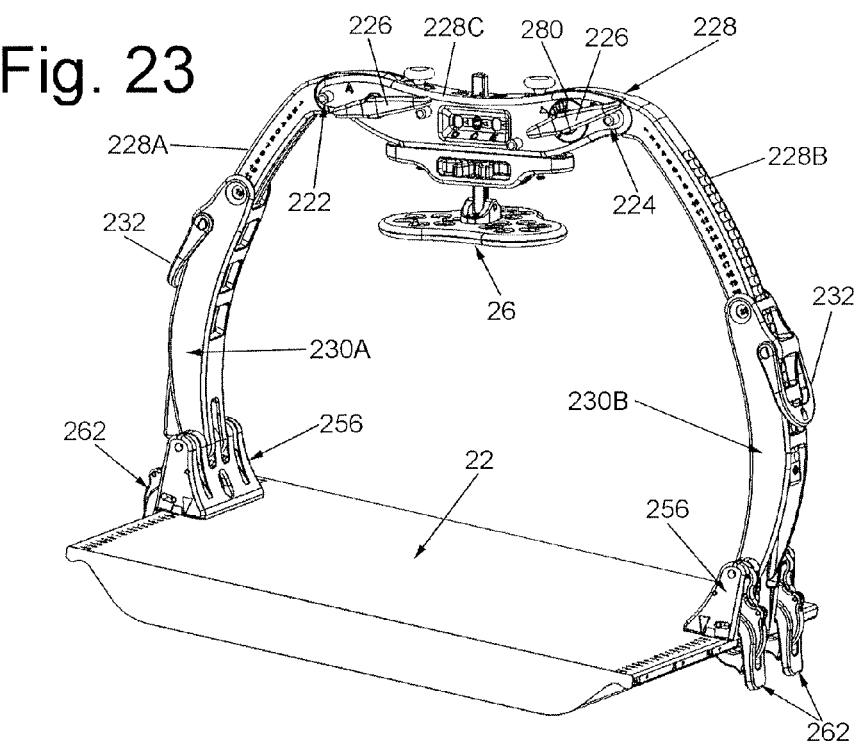
FIG. 23 is somewhat reduced isometric view of the bridge device shown in FIG. 22, but viewed from the rear side of the bridge device.

Referring now to FIG. 22, another, and more preferred, exemplary embodiment of a bridge device 220 constructed in accordance with this invention is shown. The bridge device 220 is configured to be mounted on the exemplary patient support panel 22 of a patient positioning system like that described above. Thus, in the interest of brevity the details of the patient support panel will not be reiterated and the common components will be given the same reference numbers.

The bridge device 220, like the bridge device 20 described above, is arranged to mount or support a multitude of positioning/fixation devices, e.g., a chest plate 26, on it and for it to be mounted on the patient support panel 22 (via the side rails 22A and 22B) at various positions along the length of the patient support panel and not merely at any discrete indexing points established by the pairs of apertures in the side rails if the patient support panel includes such indexing apertures. The particular positioning/fixation device used is releasably mounted on a central portion of a bridge member 228 (to be described hereinafter) of the bridge device.

Figure 28:
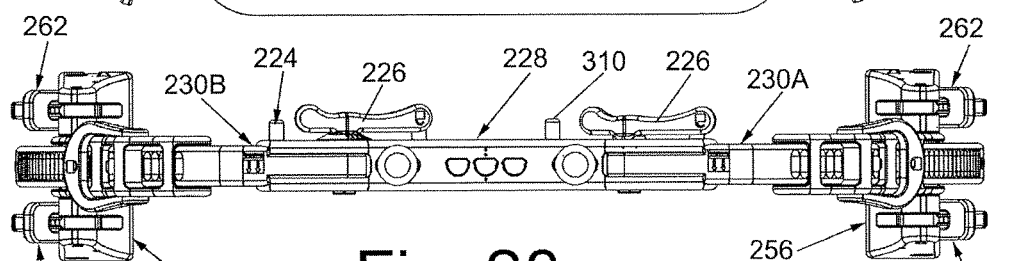
FIG. 28 is a top plan view of a bridge device like that of FIG. 22 shown without the patient support panel.
Figure 29:
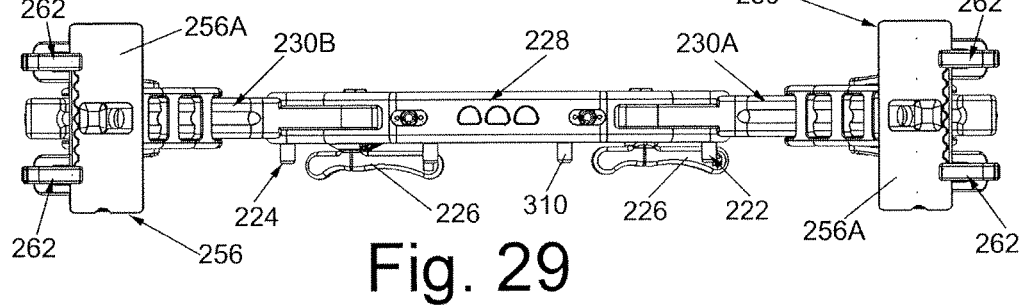
FIG. 29 is a bottom plan view of the bridge device of FIG. 28.
Figure 30A:
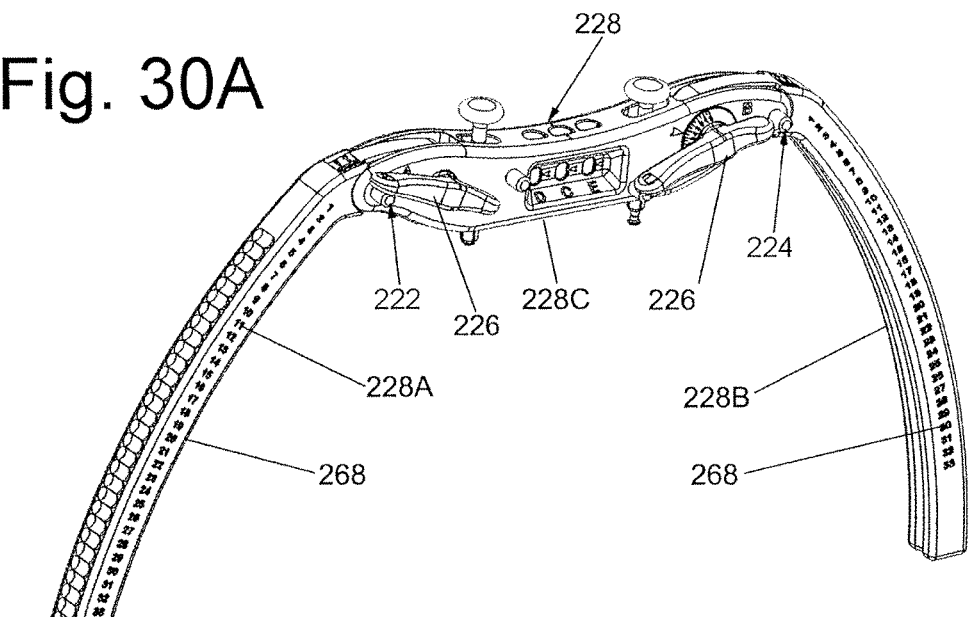
FIG. 30A is an isometric view of the bridge member of the bridge device shown in FIG. 22 taken from an angle showing the rear of the bridge member and with the side sections of the bridge member at an exemplary angle to the center section of the bridge member.

The bridge device 220 basically comprises a bridge member 228, a right side support assembly 230A and a left side support assembly 230B. The bridge member 228 is best seen in FIGS. 28-30 and is an assembly of various components formed of any suitable material like those used in prior art bridges for SBRT and other similar applications. In particular bridge member 228 basically comprises a tripartite assembly of an elongated and arcuate right side section 228A, an elongated and arcuate left side section 228B and an elongated and generally linear central section 228C. The central section 228C includes a right side end portion which is pivotally connected to the right side section by a right side pivot mechanism 222 (to be described later). The central section 228C also includes a left side end portion which is pivotally connected to the left side section by a left side pivot mechanism 224 (also to be described later). Both the right side pivot mechanism 222 and the left side pivot mechanism 224 include a locking or latch mechanism 226, to be described later, for releasably locking the associated side section at a desired angle to the central section of the bridge member.

The right side section 228A projects downward and outward from the right side of the central section 28C and the left side section 28B projects downward and outward from the left side of the central section 28C. Thus, the two side sections 228A and 228B can be said to flare outward and downward from their respective sides of the central section. It should be pointed out at this juncture that while the right and left side sections are preferably arcuate, it is contemplated that they may, if desired, be linear providing that they flare outward and downward from the central section, as will be appreciated from the discussion following later. The central section includes plural holes and/or slots 250 extending therethrough which serve as the mounting points for the fixation component, e.g., the chest plate 26, to be mounted on the bridge member 228.

Figure 24:
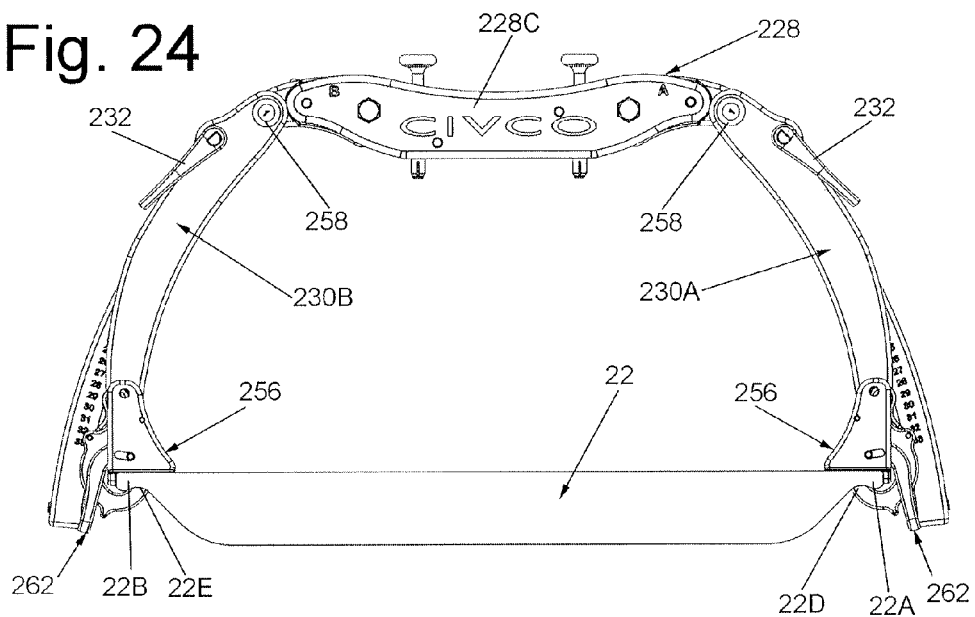
FIG. 24 is a front elevation view of the device like shown in FIG. 22, but with the bridge member in its lowermost and centered position over the patient support panel and with the center portion of the bridge member extending generally parallel to the plane of the patient support panel.
Figure 25:
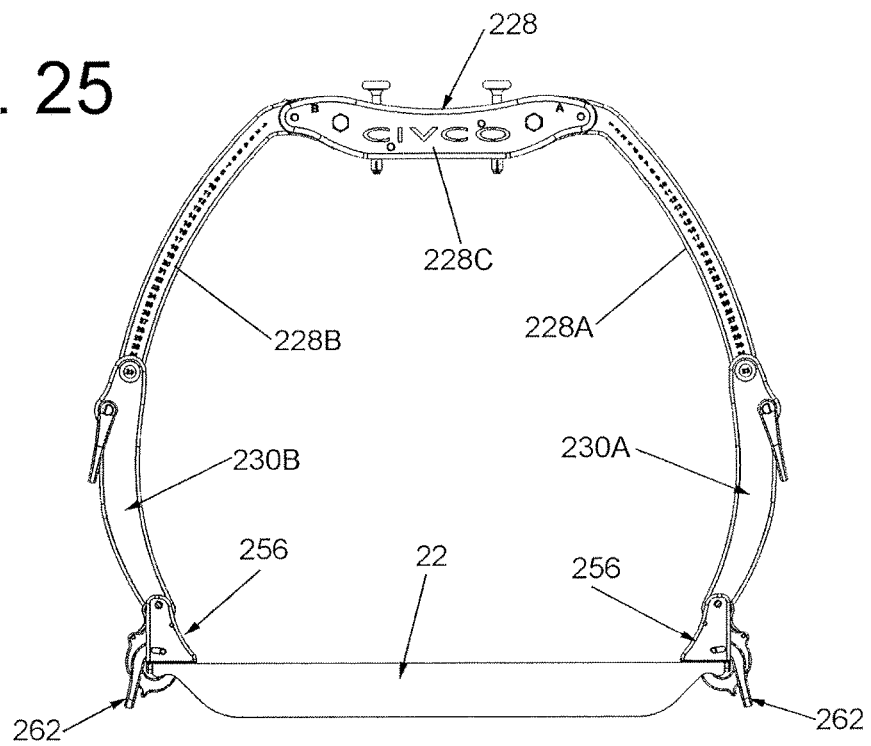
FIG. 25 is a front elevation view of the bridge device like shown in FIG. 24, but with the bridge member in its uppermost or highest centered position over the patient support panel and with the center portion of the bridge member extending generally parallel to the plane of the patient support panel.

Providing side sections 228A and 228B, which are pivotally connected and angled with respect to the central section as just mentioned, effectively increases the length that they can travel with respect to their respective side support assemblies 230A and 230B, for any given elevation of the central section 228C above the patient support panel 22. Thus, the bridge device 220, like the bridge device 20, permits a greater range of adjustment than prior art bridges. In particular, the angled side sections 228A and 228B enable one to achieve a maximum height of the central section 228C of the bridge member with respect to the patient support panel 22, such as shown in FIG. 25, while enabling that section to be set at the lowest position with respect to the patient support panel, such as shown in FIG. 24, without the free ends of the side sections 228A and 228B extending substantially below the patient support panel 22. Moreover, the angling inward of the side sections from their free distal end to the portion at which they pivotally connect to the central section enables the bridge member 228 to be readily accommodated within a circular area, such as the bore of the treatment apparatus, e.g., the LINAC, MRI, CT scan apparatus, or the gantry which encircles the patient during the treatment. Further still, making the side sections arcuate and enabling them to pivot with respect to the central section, as will be described later, provides even greater space within the bounds of the bridge device for the patient and can closely fit within the bore of the treatment apparatus when the bridge is set in its maximum extended position.

Turning now to FIGS. 30A-31E the details of the right side pivot mechanism 222 and the left side pivot mechanism 224 will now be described. As mentioned above both side pivot mechanisms 222 and 224 include a locking or latch mechanism 226 for releasably locking the associated side section at a desired angle to the central section of the bridge member. The left side pivot mechanism 224 also includes an indicator assembly 280, to be described later, for indicating the particular orientation at which the left side section 228B is disposed with respect to the left side of the central section 228C. The pivot mechanisms 222 and 224 are identical in construction except for the indicator mechanism 280 associated with the left side pivot mechanism. Thus, in the interest of brevity only one of the side pivot mechanisms, i.e., left side mechanism 224, will be described.

Figure 30B:
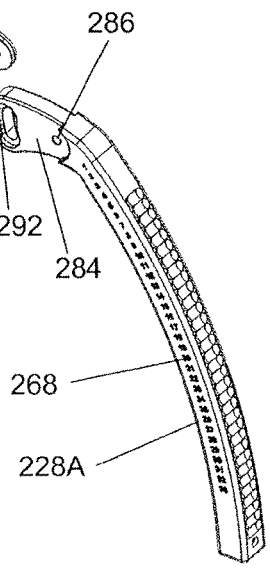
FIG. 30B is an exploded isometric view of the bridge member shown in FIG. 30A, but taken from a different direction, e.g., showing the front of the bridge member.
Figure 30C:
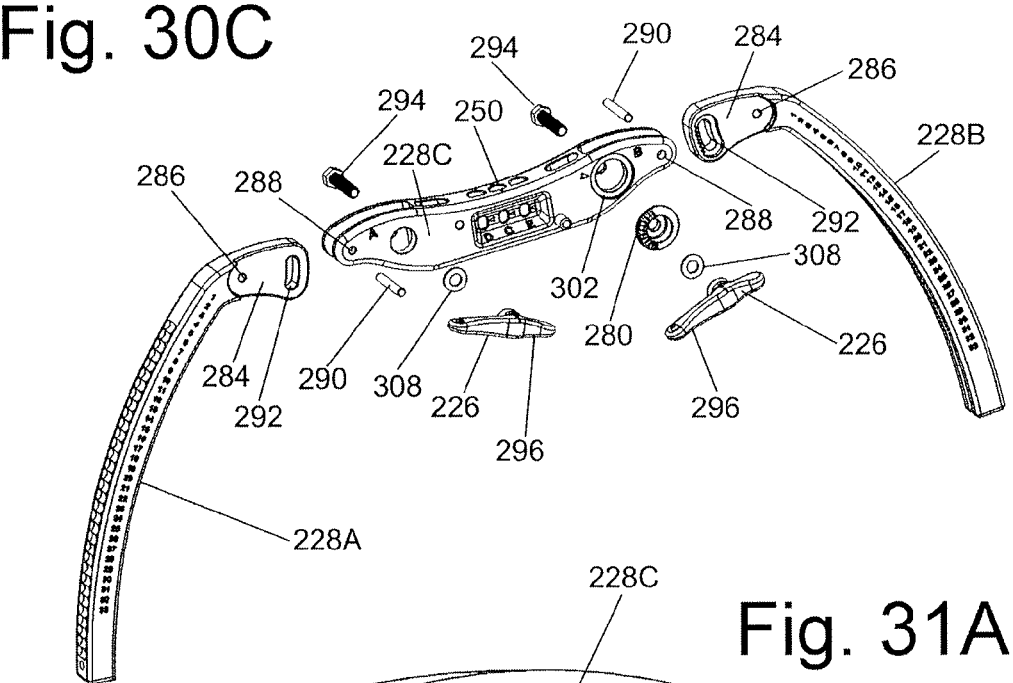
FIG. 30C is a slightly reduced size exploded isometric view of the bridge member shown in FIG. 30B, but taken from a different direction, e.g., showing the rear of the bridge member.

The left side mechanism basically comprises a pivot pin 290 and the left side of the central section 228C, which as can be seen clearly in FIGS. 30B and 30C is in the form of a yoke 282. The upper end 284 of the left side section 228B is enlarged (e.g., flared) and of a thickness sufficient to fit closely within the yoke 282. A hole 286 extends through the flared end 284. A pair of axially aligned holes 288 extend through the sides of the yoke and are axially aligned with the hole 286 when the flared end 284 of the left side section 228 is within the yoke. The pivot pin 290 extends through the aligned holes. A bearing sleeve can be provided interposed between the holes and the pivot pin. Thus, the left side section can pivot with respect to the left side of the central section about the axis of the pivot pin 290.

Figure 31A:
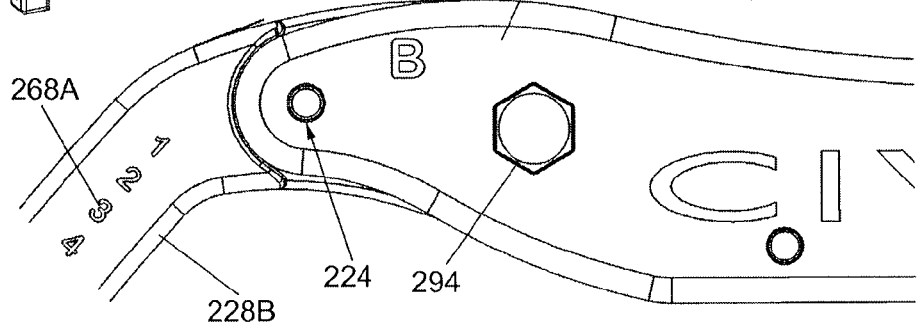
FIG. 31A is an enlarged front elevation view of a portion of the bridge member shown in FIGS. 30A-30C.
Figure 31B:
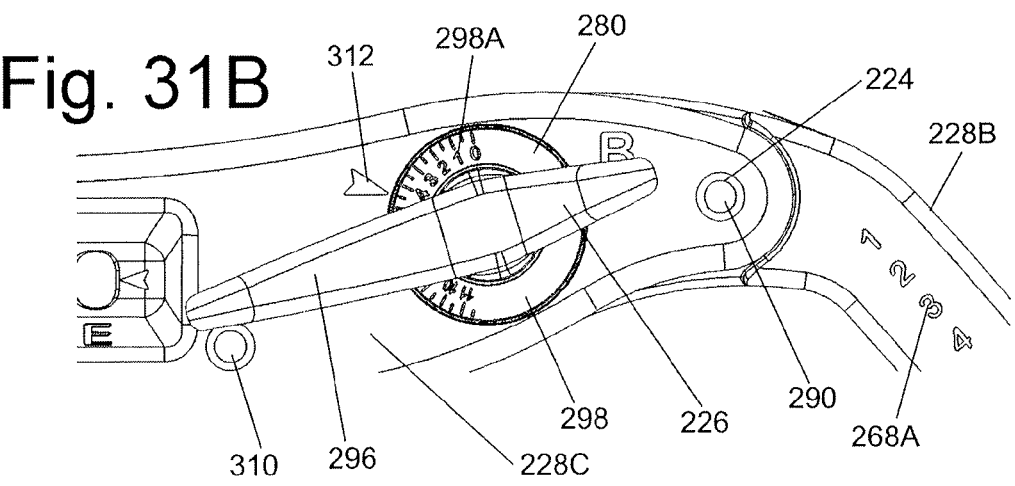
FIG. 31B is a rear elevation view of a the portion of the bridge member shown in FIG. 31A.

The range of angles through which the left side section can be pivoted is limited by a stop mechanism. In particular, as best seen in FIG. 31D, the flared end portion 284 at the upper end of the left side section includes an arcuate track or slot 292. The slot 292 is adapted to receive a portion of a hex-head bolt 294 extending therethrough. The head of the bolt is arranged to be received within a correspondingly shaped recess in the front wall at the of the left side end of the central section to prevent the bolt from rotating about its central longitudinal axis. The bolt forms a component of the heretofore identified latch mechanism 226. That mechanism also includes a lever or handle 296 which is threadedly connected to the end of the bolt that is located opposite the bolt's head. The lever or handle 296 is arranged to be pivoted about the axis of the bolt in the clockwise direction to cause the portions of the inner surface of the yoke at the left side end of the central section 228C to frictionally engage the flared end portion of the left side section 228B and thereby releasably lock that section to the central section at whatever the angle set. Conversely, the rotation of the lever or handle 296 in the counter-clockwise direction releases the inner surfaces of the yoke from frictional engagement with the flared end portion of the left side section 228D to enable the left side section to pivot about the pivot pin 290 with respect to the central section. Since the shaft of the bolt is located in the arcuate slot 290 the ends of the slot act as stops thereby establishing or limiting the angular range through which the left side section can be pivoted with respect to the central section.

As mentioned above, the latch or locking mechanism 226 includes an indicator assembly 280 to provide a visual indication of the particular orientation that the left side section 228B is with respect to the central section 228C. That mechanism 226 basically comprises an index (indicator) wheel or disk 298 having indicia 298A (FIG. 31B) extending about a portion of the outer surface of the disk. That indicia comprises lines and associated number (e.g., 0-11). The disk 298 includes a cylindrical central hub 300 (FIG. 31E) which extends through a circular opening 302 in one side of the yoke at the left end of the central section 228C. The inner end of the hub 300 is in the form of a toothed gear 304. The teeth of the gear 304 are arranged to engage corresponding teeth of an arcuate toothed rack 306 (FIG. 31D) located in a recess in the side section 228B adjacent the arcuate slot 292 of that side section. A washer 308 is provided between the disk 298 and the lever 296 as a thrust washer reducing friction between it and the disk when securing the mechanism 226.

As should be appreciated by those skilled in the art, when the side section 228B is pivoted with respect to the central section, the arcuate rack 306 which forms a portion of that side section 228B will pivot about the axis of the pivot pin 290, whereupon the teeth of the gear 304 will roll along the rack, thereby rotating the index disk about the axis of the bolt. As best seen in FIG. 31B the front wall or surface of the central section 228C of the bridge member 228 immediately adjacent the disk 298 includes a pointer, e.g., an arrow head 312, pointing towards the disk, and thus indicating the position that the disk has been rotated to (e.g., positions 0-11) with the indicated number representing the angle of the side section to the central section. This number representing the angle can be noted and recorded for future reference, e.g., to reset the side section to that same angle. Moreover, the geometry of the indicator assembly is such that a very slight change in angle of the side section to the central section will result in a substantial rotation of the index wheel, thus providing increased resolution.

The geared connection between the index wheel and the left side section in addition to providing a high resolution indication of the angle of the left side section to the central section also provides an additional mechanical advantage for securing the angular position of the left side section with respect to the central section.

Figure 31C:
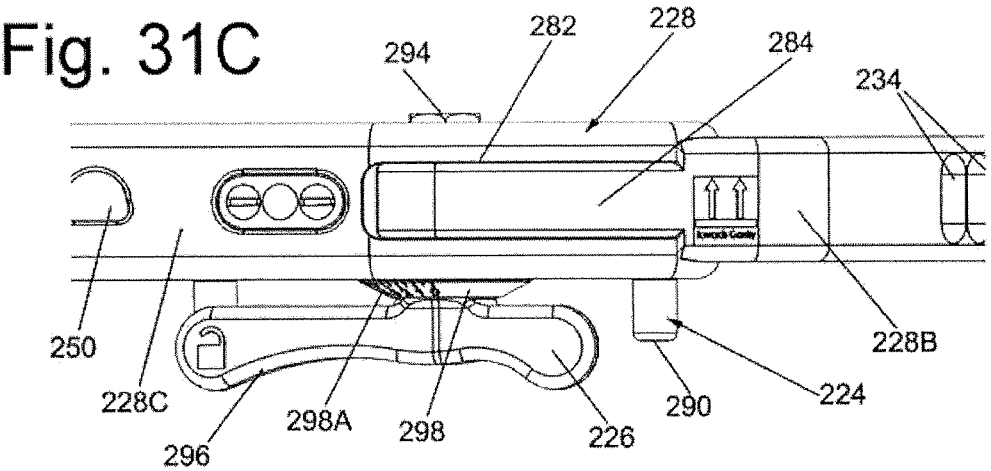
FIG. 31C is a top plan view of the portion of the bridge member shown in FIGS. 31A and 31B.
Figure 31D:
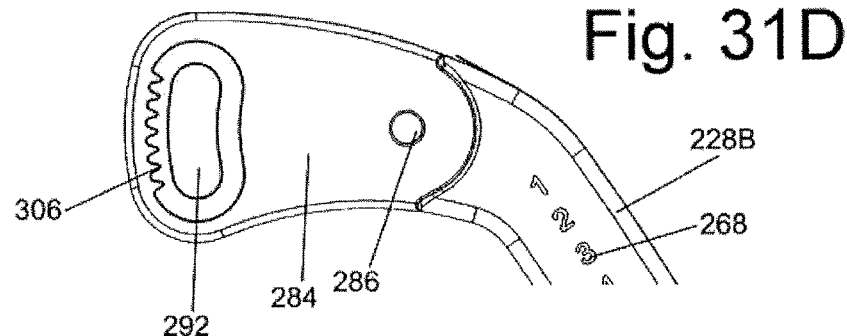
FIG. 31D is a front elevation view of a portion of the bridge member shown in FIGS. 31A-31C.
Figure 31E:
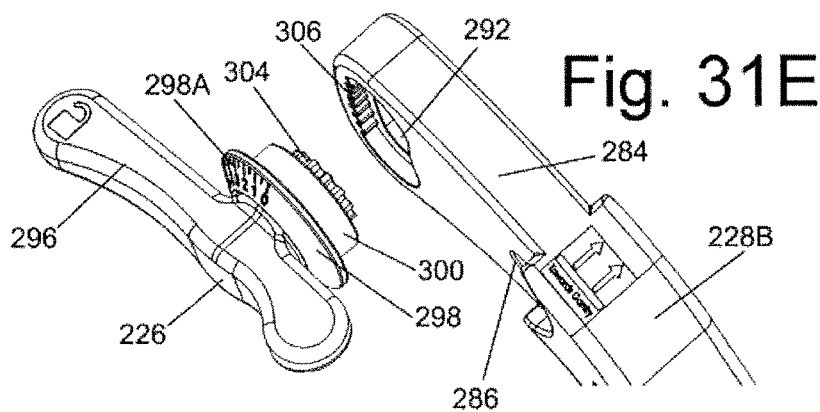
FIG. 31E is an exploded isometric view of a portion of the bridge member shown in FIGS. 31A-31C.

In order to ensure that the locking lever 296 cannot be rotated too far in the clockwise direction to lock the side section 228B in the angular orientation set, the pivot pin 290 extends out of the rear surface of the central section 228C to form a stop for the locking lever as shown in FIG. 31C. Moreover, to ensure that the lever cannot be rotated too far in the counter-clockwise direction, which could disconnect the locking lever from its bolt 294, another stop 310 is provided projecting out from the rear surface of the central section on the opposite side of the disk 298 from the pivot pin 290, as also shown in FIG. 31C.

It should be pointed out at this juncture that if desired the bridge device 220 can make use of an indicator assembly for the right side pivot assembly to provide an indication of the angle of the right side section with respect to the central section, e.g., if the user wanted to match both sides to the same angle to center the central section over the patient support panel. However, it has been determined that such centering of the bridge is typically unnecessary inasmuch as the adjustment of the height of each of the side sections to their respective support assemblies will automatically tailor the shape and orientation of the bridge member to the particular patient's anatomy (as will be described later). If, on the other hand, the additional mechanical advantage provided by the use of the indicator assembly is desired for the right side of the bridge member, notwithstanding the additional cost for inclusion of the same in the device, the right side pivot assembly 222 can be made to incorporate such an indicator assembly.

In the interest of "user-friendliness" each of the actuating levers 296 of the locking mechanisms 226 includes indicia, e.g., an icon of an unlocked padlock, to indicate the direction the lever is to be rotated to unlock the locking mechanism. An icon of a locked padlock is provided on the opposite side of each of the levers to indicate the direction that they are to be rotated to lock the locking mechanism. A similar "lock" icon is provided on one surface of the actuating lever 270 of each releasably securable connector assembly 232. A similar "unlock" icon is provided on the opposite surface of each of those actuating levers 270.

As mentioned earlier the right side section 228A of the bridge member 228 is arranged to be releasably secured to the right side rail 22A of the patient support panel 22 at various locations therealong by the right side support assembly 230A, whereupon the right side section projects in an upward direction from the right side rail. Similarly, the left side section 228B of the bridge member 228 is arranged to be releasably secured to the left side rail 22B at various locations therealong by the left side support assembly 230B, whereupon left side section projects in an upward direction from the left side rail. The central section 228C bridges the patient support panel 22 between the right and left side support assemblies.

Like the device 20, one of the significant aspects of the bridge device 220 is that the right side section of the bridge member 228 is independently adjustable in position with respect to the right side support assembly 230A, and the left side section of the bridge member is independently adjustable with respect to the left side support assembly 230B, whereupon the portion of said central section 228C at the right side section can be disposed at any one of various desired distances from the top surface of the patient support panel and the portion of the central section at left side section can be independently disposed at any one of various desired distances from the top surface of the patient support panel. In fact, as will be described later the bridge device can be adjusted to the particular patient's anatomy. For example, the patient can be disposed on the patient support panel and the fixation component, e.g., the chest plate 26, can be brought into engagement with the patient while all of the bridge device's locking mechanisms are loose, whereupon the bridge member 228 will automatically assume the position and orientation to accommodate the fixation component's engagement with the patient, i.e., each side section of the bridge member will assume the appropriate height with respect to the device's side support assemblies and each side section will assume the appropriate angle between it and the central section of the bridge member. The lock mechanisms can then be set to the lock position to hold the bridge device in that position and orientation. The details of the construction of the bridge member 228 and the side support assemblies 230A and 230B to accomplish that function will be described in detail later.

Suffice for now to state the right side support assembly 230A includes a releasably securable connector or lock assembly 232 (to be described in detail later) having a lock axle 236 (to be described later) arranged to releasably engage any one of a series of notches or grooves 234 extending along an outside portion of the side section 228A of the bridge member. In a similar manner, the side support assembly 230B includes an identical releasably securable connector or lock assembly 232 having a lock axle 236 arranged to releasably engage any one of a series of notches or grooves 234 extending along an outside portion of the side section 228B. In particular, as best seen in FIGS. 28-30, the side section 228A includes a series of notches or grooves 234 extending parallel to the longitudinal central axis 22C on the outer surface of that section. In a similar manner, the side section 228B includes a series of notches or grooves 234 extending parallel to the longitudinal central axis 22C on the outer surface of that section. The notches or grooves 234 are sequentially disposed equidistantly along the length of their respective side sections 238A and 238B.

The lock axle 236 of the releasably securable connector assembly 232 of each side support assembly is arranged to releasably lock or engage any one of the notches 234 of the associated side section of the bridge member to hold the position of the bridge member with respect to the patient support panel when the lock assembly is engaged. For example, FIG. 24 shows the bridge device 220 with its bridge member 228 in its most refracted or compact state, wherein an the lock axle 236 is aligned and releasably secured within the uppermost notch 234 in the two side sections 228A and 228B. In this state the central section 228C of the bridge member 228 is parallel to the top surface of the patient support panel 22. If the angle of each side section to the central section is the same the central section will be centered over the patient support panel, like shown, with each side of the central section 228 at the same (i.e., closest) distance from the top surface of the patient support panel.

In FIG. 25 the bridge device 220 is shown with its bridge member 228 in its most extended or expanded state, wherein the lock axle 236 of each of the respective releasably securable connectors is aligned and releasably secured within the lowermost notch 234 in the two side sections 228A and 228B. In this state the central section 228C of the bridge member is parallel to the patient support surface, is centered thereover, and each end of the central section is at the same and furthest distance from the top surface of the patient support panel.

Figure 26:
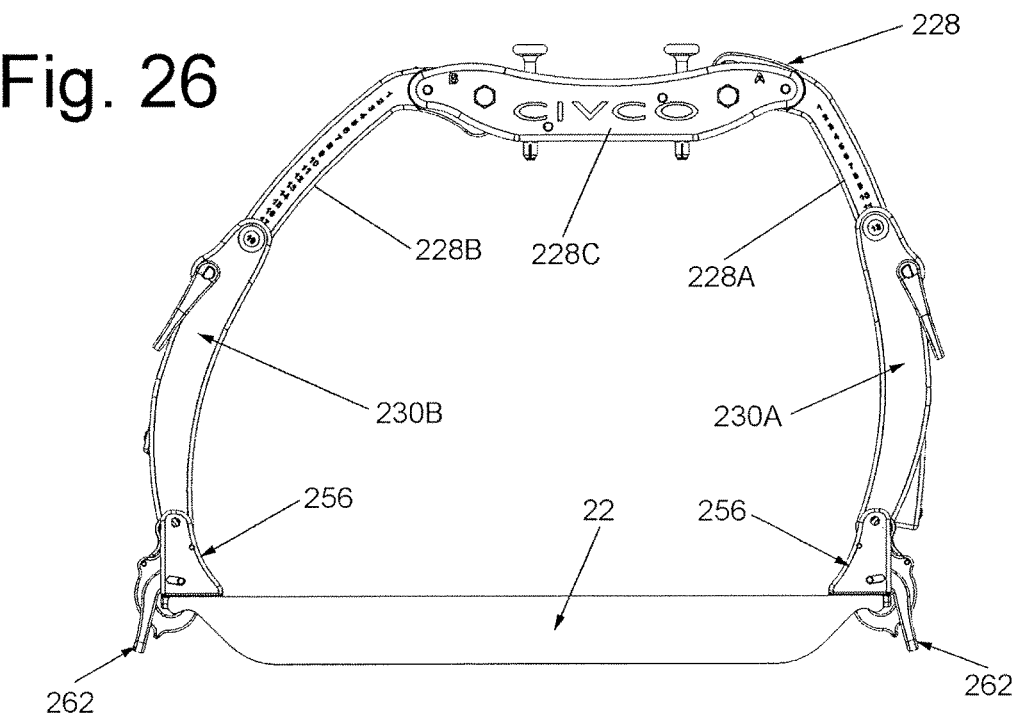
FIG. 26 is a front elevation view like shown in FIG. 22, with the bridge member in another exemplary asymmetrical position over the patient support panel and with the center portion of the bridge member extending generally parallel to the plane of the patient support panel.

In FIG. 26, the bridge device 220 is shown with its bridge member 228 in one of many exemplary asymmetrical states or orientations, i.e., the right side of the central section 28C of the bridge member is located at a shorter distance from the top of the right side support assembly 230A than the left side of the central section is located from the top of the left side support assembly 230B. However, the central section is still parallel to the top surface of the patient support panel, albeit displaced laterally, i.e., shifted to the right with respect to the patient support panel. To achieve this orientation the lock axle 236 of the right side support assembly 230A is aligned and releasably secured within a notch 234 of the right side section 228A closer to the central section 228C than the notch 234 of the left side section 228B in which the lock axle 236 of the releasably securable connector of the left side support assembly 230B is releasably secured and the angle between the right side section 228A and right side of the central section 228C is less than the angle between the left side section 228B and left side of the central section 228C.

Figure 27:
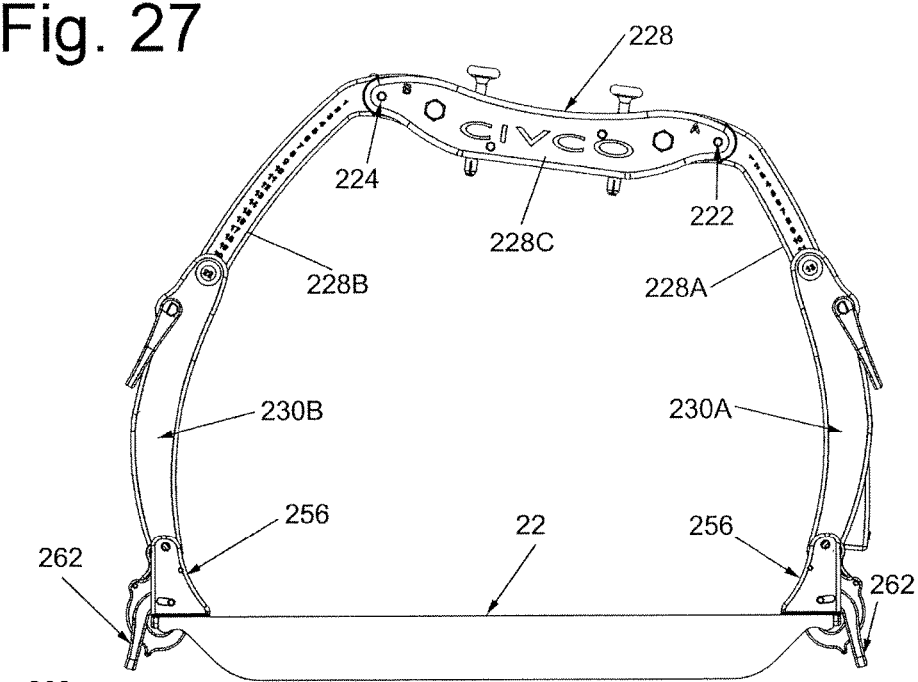
FIG. 27 is a front elevation view like shown in FIG. 26, with the bridge member in another exemplary asymmetrical position over the patient support panel and with the center portion of the bridge member extending at an angle to the plane of the patient support panel.

In FIG. 27, the bridge device is shown with the bridge member 228 in another of many exemplary asymmetrical states or orientations. In particular, in this orientation the central section 228C of the bridge member is skewed or at an acute angle to the top surface of the patient support panel. To achieve this orientation the lock axle 236 of the releasably securable connector 232 of the right side support assembly 230A is aligned and releasably secured within a notch 234 of the right side section 228A closer to the central section 228C than the notch 234 of the left side section 228B in which the lock axle 236 of the releasably securable connector of the left side support assembly 230B is releasably secured.

In order to enable the bridge device 220 to assume the various configurations shown in FIGS. 22-25, as well as any other configuration that the device is capable of assuming, the side support assemblies 230A and 230B are constructed so that they can pivot about respective axes parallel to the central longitudinal axis 22C of the patient support panel 22.

Figure 32A:
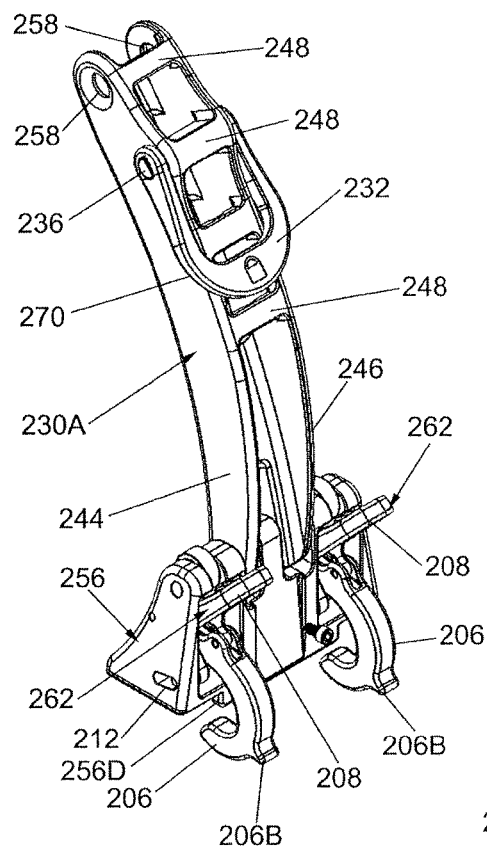
FIG. 32A an isometric view of the right side support assembly of the bridge member shown in FIG. 22.
Figure 32B:
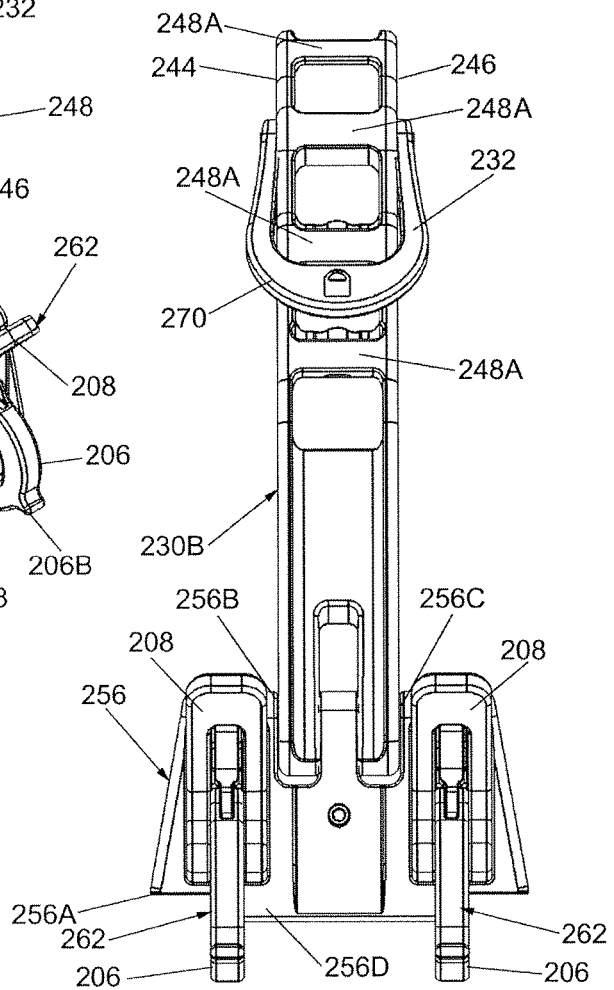
FIG. 32B is a slightly enlarged side elevation view of the right side support assembly shown in FIG. 32A.
Figure 33:
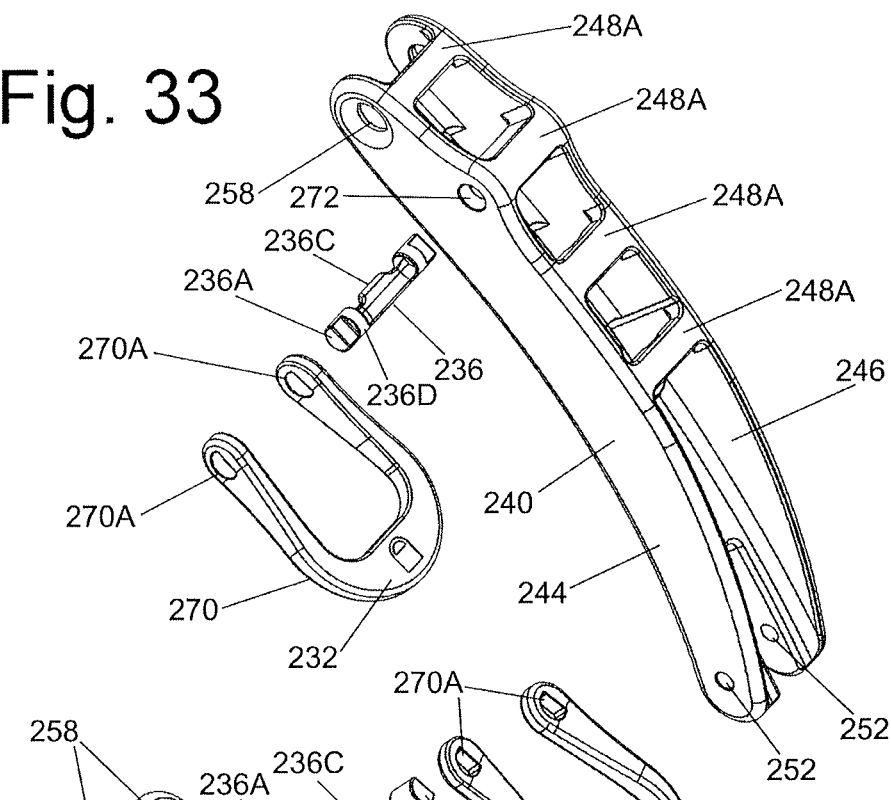
FIG. 33 is an exploded isometric view of a portion of the right side support assembly shown in FIGS. 32A and 32B taken from an outside oblique angle.
Figure 34:
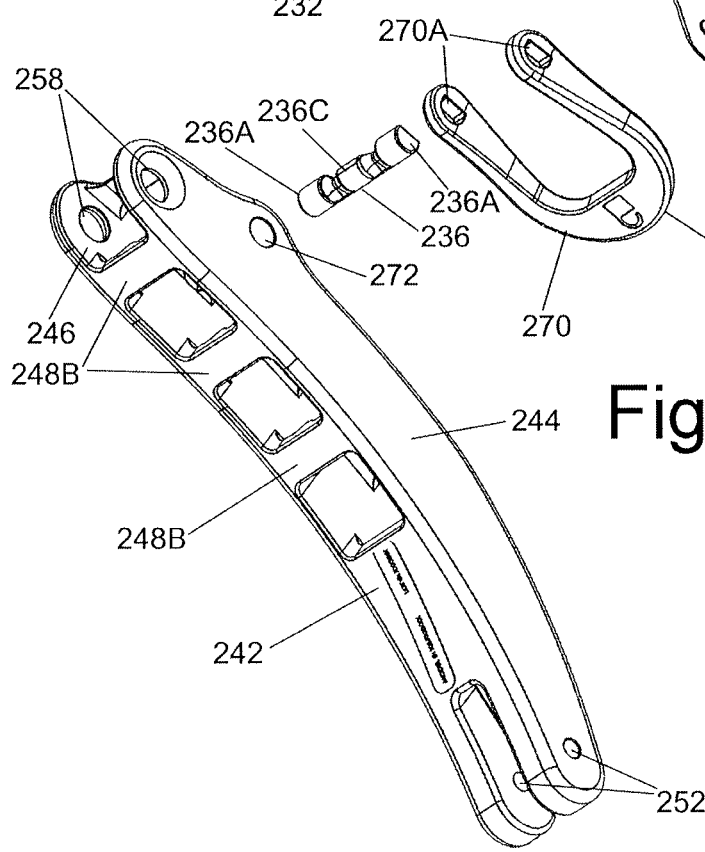
FIG. 34 is an exploded isometric view of the portion of the right side support assembly shown in FIG. 33 but taken from an inside oblique angle.

It should be pointed out at this juncture that both side support assemblies 230A and 230B are of identical construction. Thus, in the interest of brevity the details of only one of those assemblies, i.e., 230A, will be described in detail in the discussion to follow. As best seen in FIGS. 31-34 the right side support assembly 230A basically comprises an elongated, slightly arcuate, sleeve-like frame 240, a base 256 and a pair of rail clamp assemblies 262. The elongated frame 240 has a bottom wall 242 (FIG. 34), an opposed pair of sidewalls 244 and 246, four spaced-apart top bridging bars 248A and three spaced apart bridging bars 248B. The walls and bridging bars together define a channel between them which is arranged to receive the side section 228A of the bridge member 228 as best seen in FIGS. 22-27, 40 and 41. The lower end of each of the sidewalls 244 and 246 includes a respective hole 252 (FIGS. 33 and 34). The holes 252 are axially aligned and each serves to receive a respective pivot pin 254 (FIGS. 35 and 36) to pivotably connect the frame 240 to the base 256. Thus, the longitudinal axis of the pivot pin 254, which is parallel to the longitudinal axis 22C of the patient support panel, serves as the axis enabling the elongated frame 240 to pivot with respect to the base 256 about the axis of that pin.

As best seen in FIGS. 35-38 the base 256 is in the form of a member or body which includes a planar undersurface 256A, and two slots 256B and 256C in the upper portion of the body. A short height wall or flange 256D projects downward from the planar undersurface 256A at the rear of the base. The slots 256B and 256C are arranged to receive the lower end of side walls 244 and 246, respectively, of the elongated frame 240 as best seen in FIG. 32B. The pivot pin 254 extends through a central portion of the base 256, through the slots 256B and 256C and through the aligned holes 252 in the elongated frame 240 to pivotably connect the elongated frame 240 to the base 256.

The base 256 of the right side support assembly is arranged to be fixedly secured to the right side rail 22A by the pair of rail clamp assemblies 262 (whose details will be described later). The upper portion of each of the side walls 244 and 246 of the elongated frame includes a hole 258 (FIGS. 33 and 34), with those holes being axially aligned. Each of the holes 258 serves as window through which indicia 268 (FIGS. 22-27) which are provided on the front and rear surfaces of the right side section 228A can be seen. The indicia 268 constitute numbers, e.g., 1-3, which serve to indicate the point at which the lock axle 236 is with respect to the series of notches or grooves 234 and thus indicates height of that side section with respect to the patient support panel. While the indicia are shown in the exemplary embodiment as successive numbers, e.g. 1-33, they can take any form, e.g., they can be letters, colors, etc. The left side section 228B includes similar indicia.

The positioning and releasable securement of the side sections 228A and 228B of the bridge member 228 to the elongated frames 240 of the respective side support assemblies 230A and 230B is accomplished by the action of the releasable securable locking assembly 232. That action, along with the establishment of the angle(s) between the bridge member's side sections 228A and 228B and its central section 228C, fixes the shape/orientation of the bridge member 228, such as shown in the examples of FIGS. 22-27. In particular, the elongated frames 240 pivot about their respective pivot axes (the axes of their pins 254) with respect to their respective bases 256 to the orientations shown in those figures, depending upon which notch 234 of the side sections the locking mechanism 232 has engaged.

Turning now to FIGS. 33, 34 and 42A-42C, the details of the releasably securable locking assemblies 232 for locking the side sections 228A and 228B of the bridge member to the side support assemblies 230A and 230B will now be described. The releasably securable locking assembly 232 of the side support assembly 230A is of identical construction to the releasably securable locking assembly 232 of the side support assembly 230B. Thus, in the interest of brevity the details of only the releasably securable locking assembly 232 of the side support assembly 230A will be discussed. In particular, that assembly basically comprises an actuating (locking) handle or lever 270 and the heretofore mentioned lock axle 236, which are connected together as an integral unit. The actuating lever 270 is a generally U-shaped member having a pair of legs each of which includes a generally D-shaped hole 270A located at the end thereof. Each hole is arranged to receive a complementary shaped respective end of the lock axle to secure the lock axle to the actuating lever. The lock axle basically comprises a rod-like member whose end portions 236A are of circular profile having a flat so that they form the complementary D-shape to fit within the D-shaped holes 270A in the lever 270. The central portion of the lock axle 236 is necked-down at 236B and includes an outwardly projecting cam 236C at the center thereof. The portions 236D of the lock axle between the necked down region 236B and the D-shaped ends are of circular profile. The geometry of the cam 236C is designed so that its surface falls within the diameter of the circular profile portions 236D of the lock axle and in the opposite direction from the flats on the lock axle's ends. This facilitates assembly and also acts to prevent and eliminate any possible off center forces from acting on the cam portion that would cause it to rotate to the unlocked position.

The lever and lock axle unit is pivotally mounted on the elongated frame 240 of the side support assembly, via a pair of holes 272 located in the frame's side walls 244 and 246. The holes 272 are axially aligned and receive the circular profile portions 236D of the lock axle. The surface of the cam 236C is arranged to be received within any of the notches or grooves 234 in the associated side section of the bridge member 228 when the lock axle is rotated about its central longitudinal axis to its locked orientation by pivoting the actuating lever 270 downward. Moreover, the cam surface is shaped so that it acts as a detent mechanism in the groove 234 when the lever is in the locked or down position, but can be readily released by the lifting of the lever. As should be appreciated by those skilled in the art the lock axle's narrower lead geometry construction renders the lock mechanism less likely to hang up on those portions or webs of the outer surface of the bridge's side sections between the bottoms of its recesses 234. Instead with the lock axle constructed as shown it is much more inclined to self-center, thereby making locking easier for the user and rendering the locking axle resistant to breakage upon repeated use.

Turning now to FIGS. 35-39 the details of the rail clamp assemblies 262 for locking the side support assemblies 230A and 230B at any longitudinal position along the side rails 22A and 22B will now be described. It must be pointed out at this juncture that the pair of rail clamp assemblies 262 of each side support assembly 230A and 230B is of identical construction. Thus, in the interest of brevity the details of only one of those pairs of rail clamp assemblies, i.e., the rail clamp assemblies of right side support assembly 230A, will be described in the discussion to follow. To that end, each rail clamp assembly 262 basically comprises a generally C-shaped clamp member 206, an actuating lever or handle 208 and a bias spring 210. The base 256 includes a pair of slots 256E and 256F (FIGS. 35 and 36), with slot 256E being located laterally outside of slot 256B and with slot 256F being located laterally outside of slot 256C. The slot 256E communicates with a cavity 256G in the rear portion of the base 256. The slot 256F communicates with a cavity 256H in the rear portion of the base 256.

A slightly elongated slot 212 is located in each of the two outer sides of the base 256. For example as shown clearly in FIG. 37 one slot 212 is located in one side of the base and in communication with the cavity 256G. Another similarly shaped slot 212 is located in the other side of the base and in communication with the cavity 256H. A third similarly shaped slot 212 is located on the opposite side of the cavity 256G and a fourth similarly shaped slot 212 is located on the opposite side of the cavity 256H. All of the slots are axially aligned. Thus both slots 212 that are in communication with the cavity 256G are axially aligned and both slots 212 that are in communication with the cavity 256H are axially aligned. The slots 212 contiguous with the cavity 256G are arranged to receive respective ends of a slidable pivot pin 214 for slidably and pivotally mounting one of the actuating levers 208 within the cavity 256G. In a similar manner the slots 212 contiguous with the cavity 256H are arranged to receive respective ends of another slidable pivot pin 214 for slidably and pivotally mounting the other of the actuating levers 208 within the cavity 256H.

Figure 39:
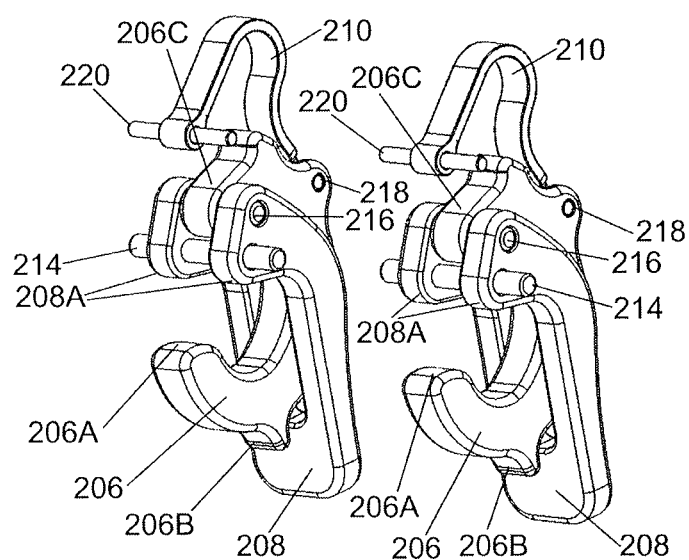
FIG. 39 is an isometric view of the clamp assemblies shown in FIG. 38, but without the base.
Figure 40:
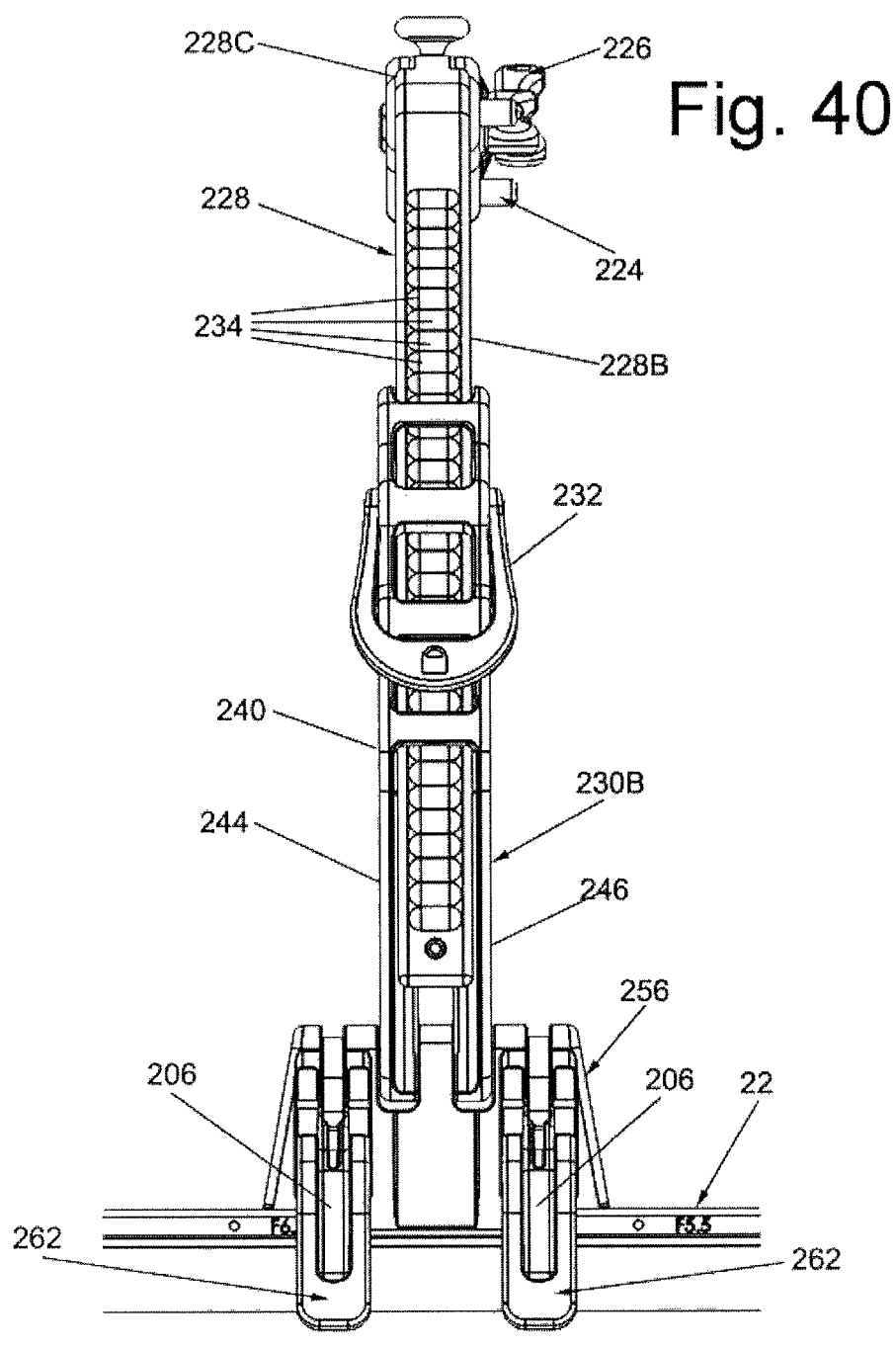
FIG. 40 is an enlarged side elevation view taken from the left side of a bridge device like shown in FIG. 22, with the bridge member being shown in an intermediate height position between the positions shown in FIGS. 24 and 25 and with the left side of the bridge member being shown in its locked state.
Figure 41:
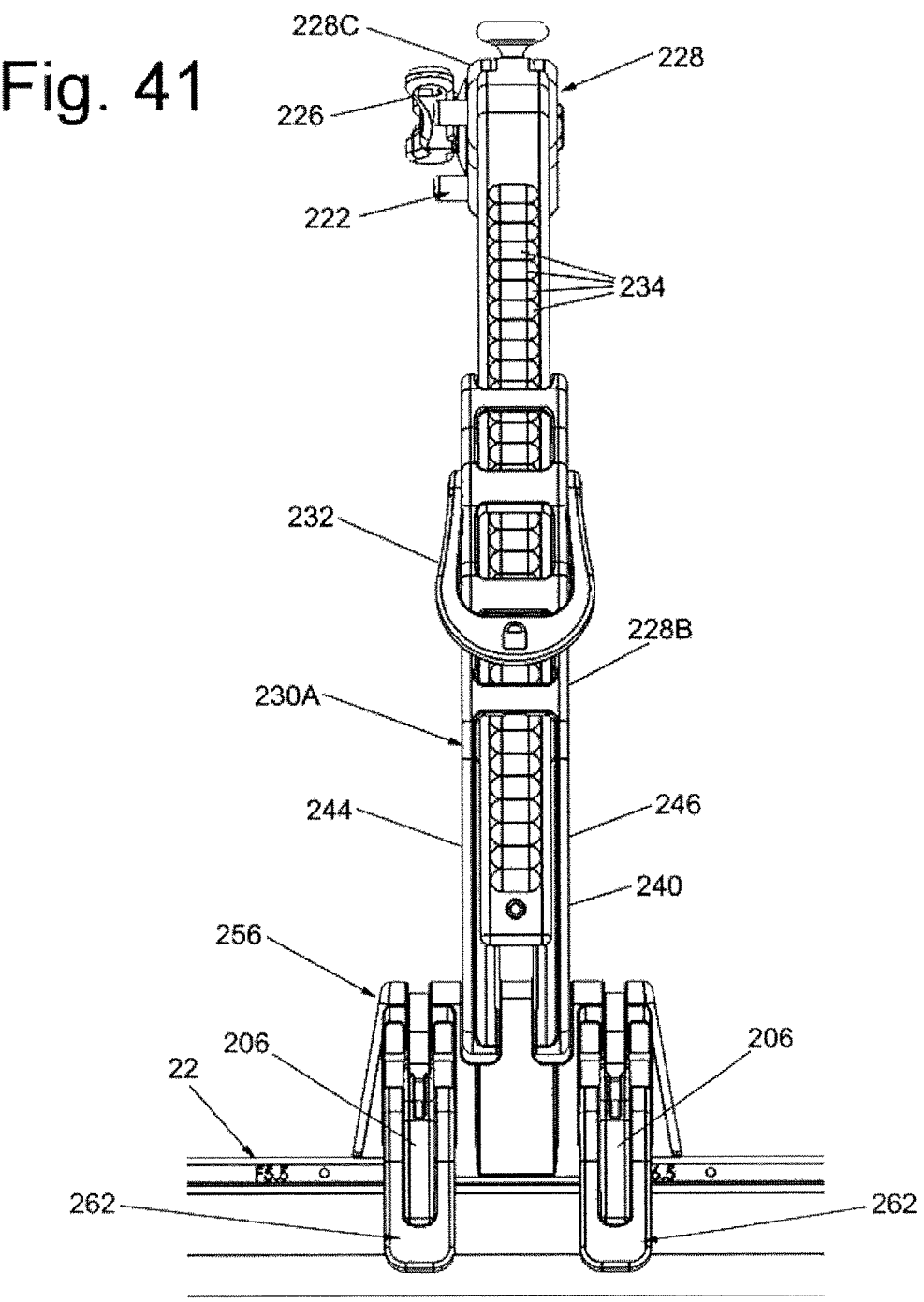
FIG. 41 is an enlarged side view taken from the right side of the bridge device shown in FIG. 40, with the right side of the bridge device being shown in its locked state.
Figure 42A:
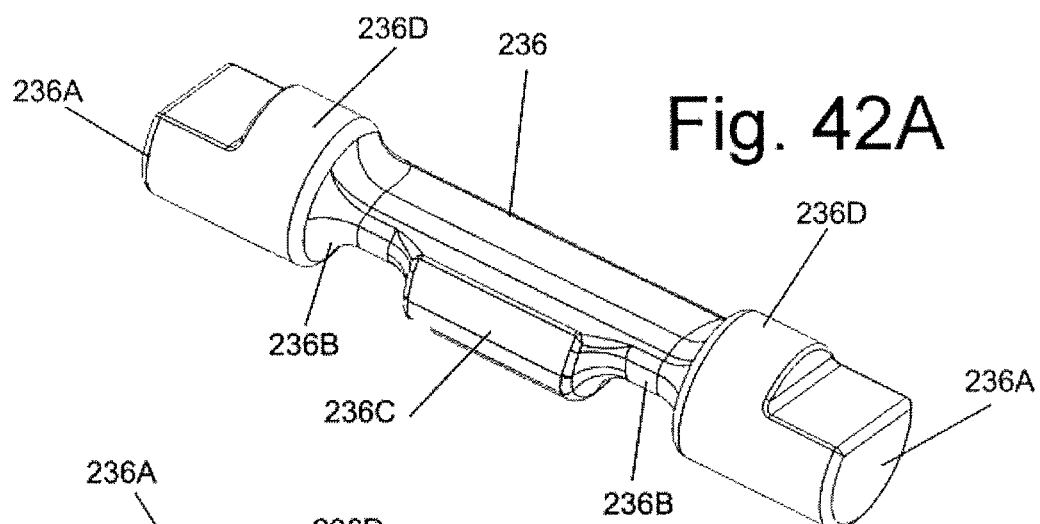
FIG. 42A is an enlarged isometric view of a lock axle forming a portion of the releasably securable locking assembly of the right side support assembly.
Figure 42B:
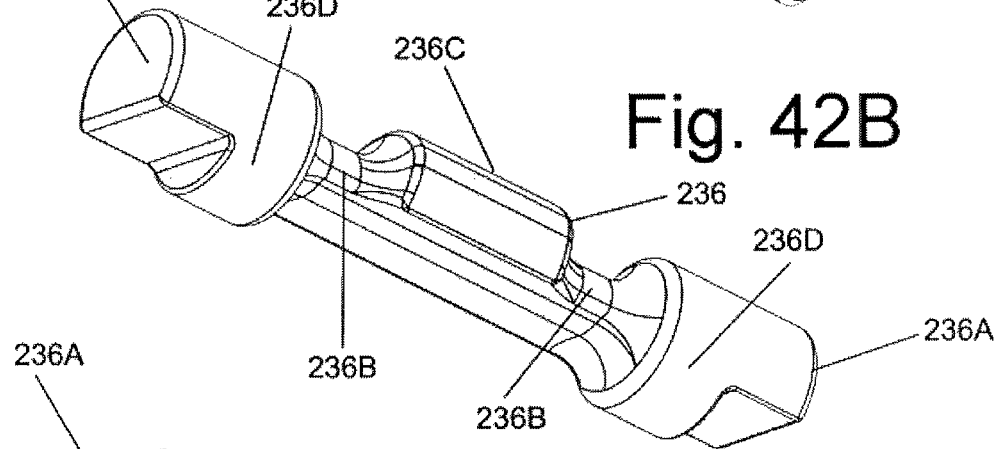
FIG. 42B is an isometric view of the lock axle shown in FIG. 42A, but taken from a different angle.
Figure 42C:
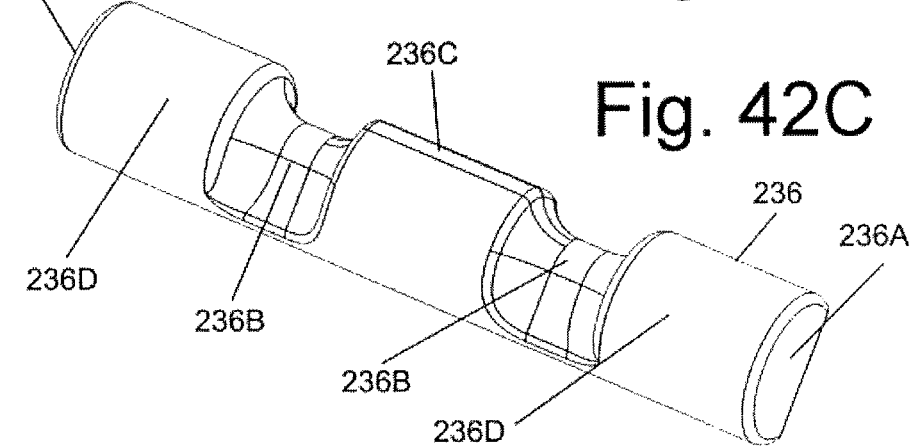
FIG. 42C is an isometric view of the lock axle shown in FIGS. 42A and 42B, but taken from a different angle.

As best seen in FIG. 39 each handle or lever 208 is a yoke-shaped member having a pair of legs, each terminating an enlarged upper end 208A. Each enlarged upper end of each lever includes a hole through which a respective end of the associated pivot pin 214 extends, with the free ends of those pivot pins being located within the slots 212 of the base. Each of the upper ends 208A of the actuating lever also includes a second hole through which a respective end of another pivot pin 216 extends. Each of the pivot pins 216 serves to pivotally mount an associated C-shaped clamp member 206 onto the associated actuating lever 208. In particular, the upper portion 206C of each of the C-shaped clamp members includes a hole through which the associated pivot pin 216 extends, with the free ends of each pivot pin 216 being located within respective second holes in the associated handle.

Each of the bias springs 210 is a resilient member which is of a curved shape and includes a lower end that is pivotally connected via an associated pivot pin 218 to an intermediate portion of an associated C-shaped clamp member 206. The upper end of each bias spring 210 is pivotally connected via an associated pivot pin 220 to the housing 256. Although it can't be seen in the figures, the portion of the base 256 on each side of each of the two cavities 256G and 256H includes a hole for receipt of a respective end of the pivot pins 220.

The top surface 206A of the bottom end of each of the C-shaped clamp members 206 is disposed opposite the planar undersurface 256A of the base 256. The undersurface 256A of the base of the right side assembly 230A is arranged to abut the top surface of the patient support panel 22 at the side rail 22A, with the inner surface of the flange 256D engaging the marginal edge of that side rail. In a similar manner, the undersurface 256A of the base of the left side assembly 230B is arranged to abut the top surface of the patient support panel 22 at the side rail 22B, with the inner surface of the flange 256D engaging the marginal edge of that side rail. The top surface 206A of each of the two C-shaped clamp members 206 is arranged to be disposed and engage the recess or groove 22D on the undersurface of the patient support panel 22 adjacent the associated side rail when the C-shaped clamp members are in their closed or lock position.

Figure 35:
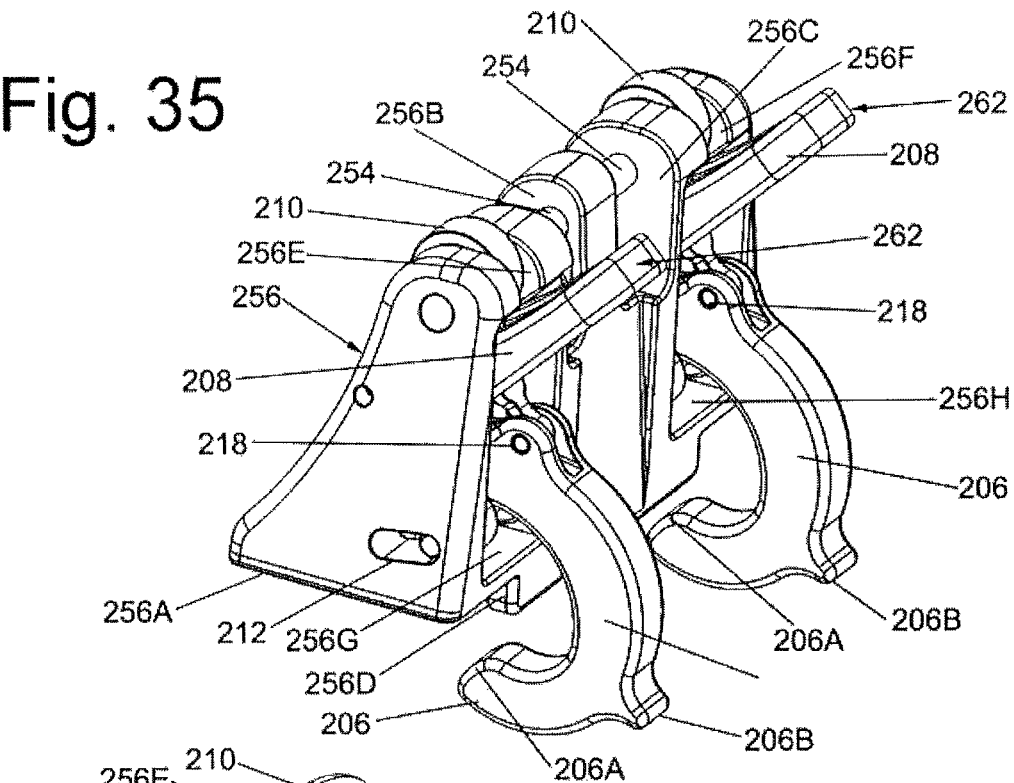
FIG. 35 is an enlarged isometric view of a portion of the right side support assembly including its base and clamp assemblies for releasably securing the right side support assembly to the right rail of the patient support panel and with the clamp assemblies being shown in their open position.
Figure 36:
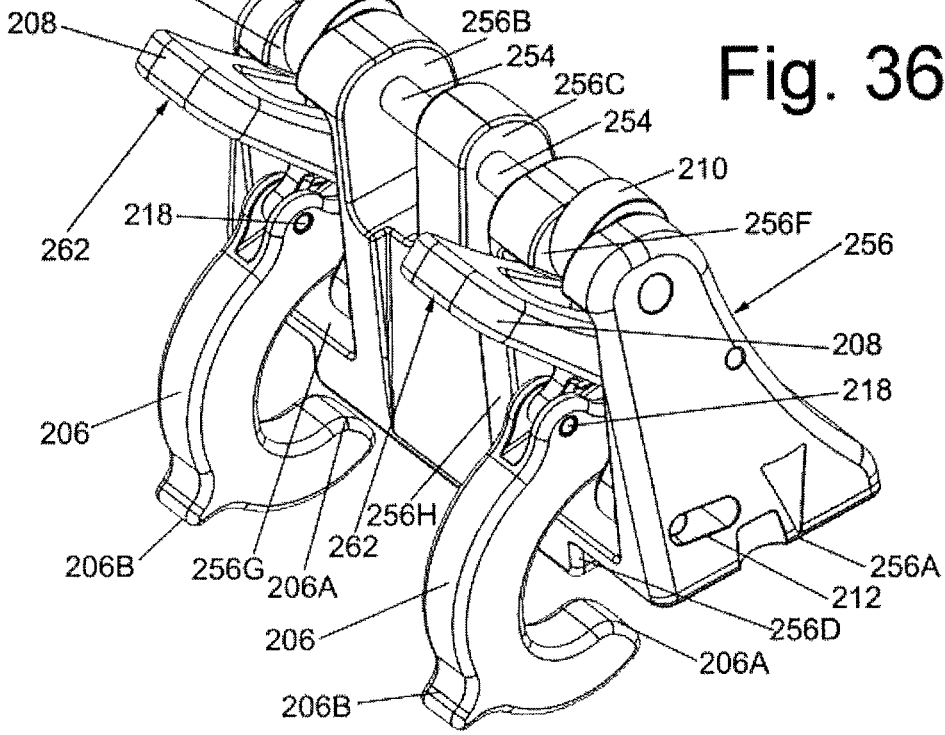
FIG. 36 is an isometric view of the base and clamp assemblies shown in FIG. 35 but taken from a different angle.
Figure 37:
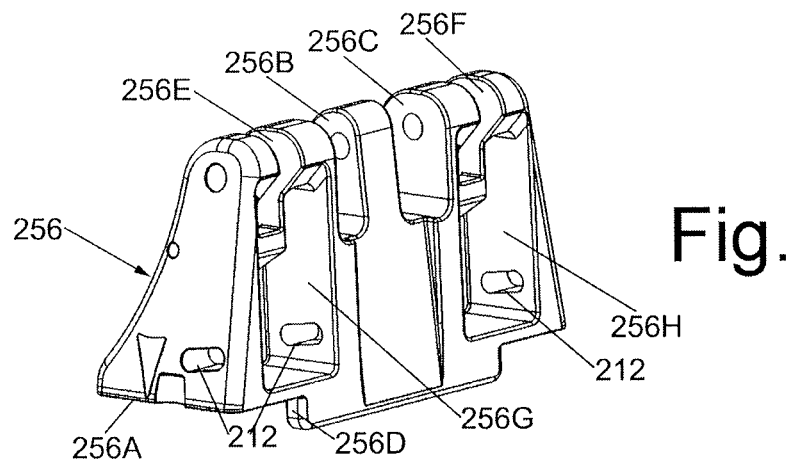
FIG. 37 is a reduced size isometric view of the base of the right side support assembly shown in FIGS. 35 and 36.
Figure 38:
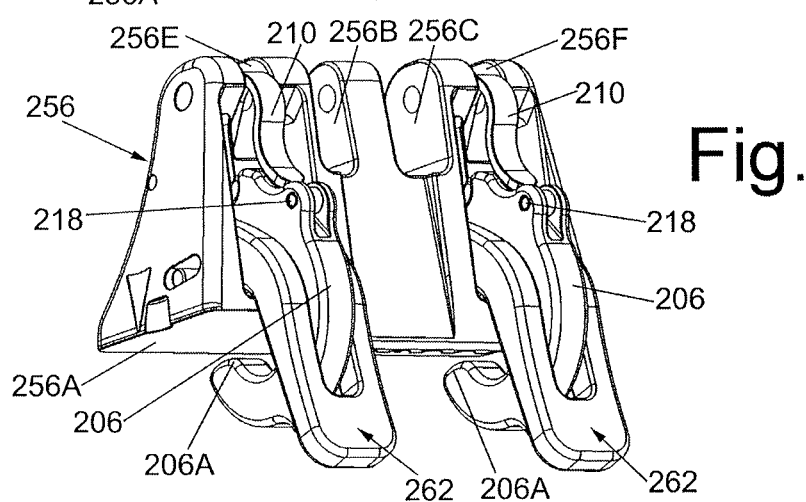
FIG. 38 is a reduced size isometric view of the base and clamp assemblies shown in FIG. 35, but taken from a different angle and with the clamp assemblies being shown in their closed position.

Each of the bias springs 210 normally applies a bias force onto the associated C-shaped clamp member 208 to bias the C-shaped clamp member (and the actuating lever coupled thereto) to the "open" position like shown in FIGS. 35 and 36. When the actuating lever 208 is rotated downward against the bias of the spring 210 it causes the C-shaped member to pivot about the axis of the pin 214, while that pin slides inward in the two slots 212 in which the ends of that pin are located to a "closed" or "lock" position. When the C-shaped clamp member is in its closed or locked position its upper surface 206A engages the groove 22D in the patient support panel and thereby tightly sandwiches the patient support panel at the location of the groove between that surface and the undersurface 256A of the base. The geometry of the upper surface 206C of each C-shaped is designed so that it bears against complimentary geometry on the inside of cavity 256G when lowering or raising the associated actuating lever 208, that along with the slot biases the lower portion of the C-shaped clamp member to swing inward or outward as the case may be.

As should be appreciated by those skilled in the art the geometry and positioning of the components of each clamp assembly 262 results in an over-center action of those components when the actuating lever of the assembly is rotated downward to the closed position, thereby releasably locking its C-shaped clamp member in the closed position against the bias of the spring. Accordingly, when all of the clamp assemblies 262 have been actuated to their lock position that action releasably locks the base of each side support assembly to the associated side rail of the patient support panel at whatever longitudinal position along the side rail the device 220 happens to be located. Conversely, rotating all the actuating levers 208 upward releases the associated C-shaped clamp members from the side rail to which the bases 256 had been secured.

In order to prevent each C-shaped clamp member from pivoting with respect to its associated actuating lever to a position which would preclude proper operation, each of the C-shaped clamp members includes a projection 206B on its outer surface. The projection 206B acts as a stop for engaging the portion of the handle at the bottom of the yoke to prevent the C-shaped clamp member from pivoting outward beyond the handle if something should accidentally push against the bottom portion of the C-shaped clamp member in an outward direction when the bridge device 220 is free, e.g., not mounted on a patient support panel.

In use, when the patient is in position on the top surface of the patient support panel 22, like shown in FIG. 1, each of the two side support assemblies 230A and 230B of the bridge device 220 can be placed on the patient support panel by moving the actuating lever or handle 208 of each of its rail clamp assemblies 262 to the position wherein its C-shaped clamp members are open. The two side support assemblies 230A and 230B can then be placed on their respective side rails of the patient support panel at the desired longitudinal position along the length of the patient positioning panel and not merely at the discrete indexing points established by the pairs of apertures (if any) in the side rails. Once the side support assemblies 230A and 230B are at their desired position on the side rails, their releasably securable connector assemblies 232 are then moved to their open state, if they are not already in that state and the locking mechanisms 226 of the bridge member 228 are set to their open or unlocked state.

The height, lateral position and angle of the central section 228C of the bridge member 228 with respect to the patient support panel can then be established. This is accomplished by bringing the patient engagement member, e.g., the chest plate 26, into engagement with the particular portion of the patient to be engaged and then sliding the side sections 228A and 228B of the bridge member 228 with respect to the associated elongated frame 240 until the desired notch 234 in that side section is aligned with the lock axle 236 of the associated releasably securable connector assembly 232. The angle at which the right side section 228A extends with respect to the central section 228C of the bridge member can then be established by pivoting the right side section 228A with respect to the central section 228C about pivot pin 290. The engagement between the teeth 304 of the indicator wheel 298 and the teeth 306 of the arcuate rack at the flared upper end of the left side section 228B causes the indicator wheel to rotate to indicate the angular position being set. Pivoting of the left side section 228B with respect to the central section 228C will automatically cause the right side section 228A to correspondingly pivot with respect to the central section 228C about its pivot pin 290 connecting the right side section to the central section.

Once the position, orientation and angle of the bridge member 228 has been established to accommodate the particular patient's anatomy, the two handles or levers 296 of the releasably securable locking assemblies 226 can be rotated to lock the side sections 228A and 228B at their respective angles to the central section 228C. Moreover, each latch lever 270 of each of the releasably securable connector assemblies 232 can be rotated downward to force the cam surface of the associated lock axle 236 into the aligned groove 234 of the associated side section of the bridge member and thereby releasably secure the frame 240 of the side support assemblies 230A and 230B to the side sections 228A and 22B, respectively at the heights established thereby.

It should be pointed out at this juncture that the sequence for mounting and adjusting the bridge device need not be accomplish in the manner as described above.

It should also be noted that any of a number of patient engagement components may be releasably mounted to the central section 228C of the bridge member. To that end, the bridge member includes plural openings 250 to which such components can be connected.

As should be appreciated from the above discussion the bridge devices of this invention provide various advantages over the prior art. For example, a single bridge device constructed in accordance with this invention can provide the same range of vertical adjustments as three prior art bridges. Thus, one bridge device can do the work of three, thereby resulting in decreased equipment costs and storage costs. Moreover, the subject bridge device is able to shift laterally, independent of the patient support panel or platform. This feature is important for locating the lesion to be treated in the isocenter of the treatment apparatus. In addition, each side of the bridge devices of the subject invention is vertically adjustable independently to allow the angle of the central section of the bridge member to vary relative to the surface of the patient support panel or platform in the plane of the bridge. This feature is important to better accommodate variations in patient rotation. Moreover, the bridge devices of this invention are able to expand laterally as the elevation of its bridge member is increased. That feature can be of considerable importance in order to accommodate large patients, since the ability to expand laterally with the elevation of the bridge member accommodates the natural tendency of thicker patients to also be wider.

It must be pointed out that the exemplary configurations of the bridge device shown in the figures of this application are merely exemplary of a myriad of different positions and configurations that bridge members constructed in accordance with this invention are able to assume. It should be pointed out at this juncture that the embodiment as shown and described above are merely exemplary of various embodiments contemplated within the scope of this invention.

Without further elaboration the foregoing will so fully illustrate our invention that others may, by applying current or future knowledge, adopt the same for use under various conditions of service.

The invention claimed is:

1. A bridge device for use with a patient positioning system, the patient positioning system including a patient support panel, a right side rail and a left side rail, said right and left side rails extending along and parallel to a central longitudinal axis of the patient support panel, said bridge device comprising a bridge member, a right side support assembly, and a left side support assembly, said bridge member comprising a right side section, a left side section and an elongated central section connected between said right side section and said left side section, said right side section being configured to be releasably secured to the right side rail at various locations therealong by said right side support assembly, whereupon said right side section projects in an upward direction from the right side rail, said left side section being configured to be releasably secured to the left side rail at various locations therealong by said left side support assembly, whereupon said left side section projects in an upward direction from the left side rail with said central section extending over the patient support panel, wherein said right side section comprises a right side contiguous arcuate portion and is adjustable with respect to said right side support assembly, wherein said left side section comprises a left side contiguous arcuate portion and is adjustable with respect to said left side support assembly, wherein said right side section of said bridge member includes a plurality of notches extending along at least a portion of the length thereof, wherein said left side section of said bridge member includes a plurality of notches extending along at least a portion of the length thereof, wherein said right support assembly comprises a clamp member configured to be releasably disposed in any one of said notches in said right side section of said bridge member to releasably secure said right side support assembly to said right side section of said bridge member, wherein said left support assembly comprises a clamp member configured to be releasably disposed in any one of said notches in said left side section of said bridge member to releasably secure said left side support assembly to said left side section of said bridge member, wherein said right and left side contiguous arcuate portions are configured such that extending either of said left or right side sections along their respective right or left side support assemblies causes the bridge device to expand both vertically and horizontally with respect to said central longitudinal axis, and wherein said central section is configured to be disposed to any one of plural possible positions by movement of either one or both of said left and right side sections with respect to their respective left or right side support assemblies.

2. The bridge device of claim 1 wherein said central section of said bridge member is configured to be shifted laterally with respect to the central longitudinal axis.

3. The bridge device of claim 1 wherein said right side section of said bridge member is pivotable with respect to said central section about an axis that is parallel to the central longitudinal axis and said left side section of said bridge member is pivotable with respect to said central section about an axis that is parallel to the central longitudinal axis.

4. The bridge device of claim 1 wherein said right side support assembly comprises a right section that is configured to be pivoted about an axis parallel to said central longitudinal axis to an angular orientation with respect to the patient support panel and said left side support assembly comprises a left section that is configured to be pivoted about an axis parallel to said central longitudinal axis to an angular orientation with respect to the patient support panel.

5. The bridge device of claim 4, wherein said bridge device comprises a first lock mechanism for fixedly locking said right section of said right side support assembly in its angular orientation and a second lock mechanism for fixedly locking said left section of said left side support assembly in its angular orientation.

6. The bridge device of claim 5 wherein said lock mechanisms are located at said central section of said bridge member.

7. The bridge device of claim 4 wherein said right support assembly includes a clamp for releasable securement to the right side rail of the patient support panel and wherein said left support assembly includes a clamp for releasable securement to the left side rail of the patient support panel.

8. The bridge device of claim 7 wherein the patient support panel includes a surface having an elongated recess extending parallel to the central longitudinal axis adjacent the right side rail and an elongated recess extending parallel to the central longitudinal axis adjacent the left side rail, and wherein said clamp of said right support assembly is configured to releasably engage the elongated recess adjacent the right side rail and said clamp of said left support assembly is configured to releasably engage the elongated recess adjacent the left side rail.

9. The bridge device of claim 4 wherein said central section of said bridge member can be oriented at a desired angle to the patient support panel.

10. The bridge device of claim 1 wherein said central section of said bridge member is configured to releasably mount a fixation component thereon to enable the fixation component to engage a portion of a patient disposed on the patient support panel.

11. The bridge device of claim 1, wherein said right side member has a free end and said left side member has a free end, said free end of said right side member being located closely adjacent said right side support assembly irrespective of the notch in which the clamp member of said right side support assembly is disposed, said free end of said left side member being located closely adjacent said left side support assembly irrespective of the notch in which the clamp member of said left side support assembly is disposed.

12. The bridge device of claim 1 wherein said right side section of said bridge member flares outward and downward from said central section from the point at which said right side section is connected to said central section and said left side section of said bridge member flares downward and away from said central section from the point at which said left side section is connected to said central section.

13. The bridge device of claim 12 wherein said right side section is arcuate and wherein said left side section is arcuate.

14. A bridge device for use with a patient positioning system, the patient positioning system including a patient support panel, a right side rail and a left side rail, said right and left side rails extending along and parallel to a central longitudinal axis of the patient support panel, said bridge device comprising:
    a bridge member,
    a right side support assembly, and
    a left side support assembly,
    said bridge member comprising:
        an elongated right side section comprises a right side contiguous arcuate portion,
        an elongated left side section comprises a left side contiguous arcuate portion, and
        an elongated central section connected between said right side section and said left side section,
    said right side section being configured to be releasably secured to the right side rail at various locations therealong by said right side support assembly, whereupon said right side section projects in an upward direction from the right side rail,
    said left side section being configured to be releasably secured to the left side rail at various locations therealong by said left side support assembly, whereupon said left side section projects in an upward direction from the left side rail,
    said central section extending over the patient support panel, said right side section being adjustable with respect to said right side support assembly, said left side section being adjustable with respect to said left side support assembly,
    wherein said right side section of said bridge member includes a plurality of notches extending along at least a portion of the length thereof,
    wherein said left side section of said bridge member includes a plurality of notches extending along at least a portion of the length thereof,
    wherein said right support assembly comprises a clamp member configured to be releasably disposed in any one of said notches in said right side section of said bridge member to releasably secure said right side support assembly to said right side section of said bridge member,
    wherein said left support assembly comprises a clamp member configured to be releasably disposed in any one of said notches in said left side section of said bridge member to releasably secure said left side support assembly to said left side section of said bridge member,
    whereupon said central section can be shifted laterally with respect to the central longitudinal axis and
    wherein said right and left side contiguous arcuate portions are configured such that extending either of said left or right side sections along their respective right or left side support assemblies causes the bridge device to expand both vertically and horizontally with respect to said central longitudinal axis.

15. A bridge device for use with a patient positioning system, the patient positioning system including a patient support panel having a central longitudinal axis, a right side rail and a left side rail, said right and left side rails extending along and parallel to the central longitudinal axis of the patient support panel, said bridge device comprising:
- a bridge member,
- a right side support assembly, and
- a left side support assembly,
- said bridge member comprising:
  - an elongated right side section comprising a right side contiguous arcuate portion,
  - an elongated left side section comprising a left side contiguous arcuate portion, and
  - an elongated central section having a right side end connected to said right side section and a left side end connected to said left side section,
- said right side section being configured to be releasably secured to the right side rail at various locations therealong by said right side support assembly, whereupon said right side section projects in an upward direction from the right side rail,
- said left side section being configured to be releasably secured to the left side rail at various locations therealong by said left side support assembly, whereupon said left side section projects in an upward direction from the left side rail,
- said central section extending over the patient support panel, said right side section being adjustable with respect to said right side support assembly, said left side section being adjustable with respect to said left side support assembly,
- wherein said right side section of said bridge member includes a plurality of notches extending along at least a portion of the length thereof,
- wherein said left side section of said bridge member includes a plurality of notches extending along at least a portion of the length thereof,
- wherein said right support assembly comprises a clamp member configured to be releasably disposed in any one of said notches in said right side section of said bridge member to releasably secure said right side support assembly to said right side section of said bridge member,
- wherein said left support assembly comprises a clamp member configured to be releasably disposed in any one of said notches in said left side section of said bridge member to releasably secure said left side support assembly to said left side section of said bridge member whereupon the distance of said right side end of said central section to the patient support panel can be adjusted as desired and the distance of said left side end of said central section to the patient support panel can be adjusted as desired, and
- wherein said right and left side contiguous arcuate portions are configured such that extending either of said left or right side sections along their respective right or left side support assemblies causes the bridge device to expand both vertically and horizontally with respect to said central longitudinal axis.

16. A bridge device for use with a patient positioning system, the patient positioning system including a patient support panel having a central longitudinal axis, a right side rail and a left side rail, said right and left side rails extending along and parallel to the central longitudinal axis of the patient support panel, said bridge device comprising;
- a bridge member,
- a right side support assembly, and
- a left side support assembly,
- said bridge member comprising an elongated right side section comprising a right side contiguous arcuate portion, an elongated left side section comprising a left side contiguous arcuate portion and an elongated central section connected between said right side section and said left side section,
- said right side section being configured to be releasably secured to the right side rail at various locations therealong by said right side support assembly, whereupon said right side section projects in an upward direction from the right side rail,
- said left side section being configured to be releasably secured to the left side rail at various locations therealong by said left side support assembly, whereupon said left side section projects in an upward direction from the left side rail,
- said central section extending over the patient support panel whereupon an area having a height and a width is created over the patient support panel between said bridge member and said right and left side support sections, said right side section being adjustable with respect to said right side support assembly, said left side section being adjustable with respect to said left side support assembly, whereupon said width and height of said area can be adjusted as desired, and
- wherein said right and left side contiguous arcuate portions are configured such that extending either of said left or right side sections along their respective right or left side support assemblies causes the bridge device to expand both vertically and horizontally with respect to said central longitudinal axis.

17. The bridge device of claim 16, wherein said central section of said bridge member is configured to be shifted laterally with respect to the central longitudinal axis.

18. The bridge device of claim 16, wherein said right side section of said bridge member is pivotable with respect to said central section about an axis that is parallel to the central longitudinal axis and said left side section of said bridge member is pivotable with respect to said central section about an axis that is parallel to the central longitudinal axis.

19. The bridge device of claim 16, wherein said right side support assembly comprises a right section that is configured to be pivoted about an axis parallel to said central longitudinal axis to an angular orientation with respect to the patient support panel and said left side support assembly comprises a left section that is configured to be pivoted about an axis parallel to said central longitudinal axis to an angular orientation with respect to the patient support panel.

* * * * *